United States Patent
Byun et al.

(10) Patent No.: US 10,155,753 B2
(45) Date of Patent: Dec. 18, 2018

(54) 4-SUBSTITUTED-2-(5-SUBSTITUTED-1H-INDOL-2-YL)PHENOL DERIVATIVES, METHODS FOR PREPARING THE PHENOL DERIVATIVES AND PHARMACEUTICAL COMPOSITIONS FOR INHIBITING CELL PROLIFERATION AND MIGRATION INCLUDING THE PHENOL DERIVATIVES

(71) Applicants: KOREA UNIVERSITY RESEARCH AND BUSINESS FOUNDATION, Seoul (KR); Dongguk University Industry-Academic Cooperation Foundation, Seoul (KR)

(72) Inventors: Youngjoo Byun, Daejeon (KR); Chang Hoon Lee, Goyang-si (KR)

(73) Assignees: Korea University Research and Business Foundation, Seoul (KR); Dongguk University Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 15/295,293

(22) Filed: Oct. 17, 2016

(65) Prior Publication Data

US 2017/0129879 A1    May 11, 2017

(30) Foreign Application Priority Data

Nov. 9, 2015  (KR) .................. 10-2015-0156527

(51) Int. Cl.
| | | |
|---|---|---|
| *C07D 209/12* | (2006.01) | |
| *C07D 209/14* | (2006.01) | |
| *C07D 409/10* | (2006.01) | |
| *C07D 413/04* | (2006.01) | |
| *C07D 413/14* | (2006.01) | |

(52) U.S. Cl.
CPC ......... *C07D 413/14* (2013.01); *C07D 209/12* (2013.01); *C07D 209/14* (2013.01); *C07D 409/10* (2013.01); *C07D 413/04* (2013.01)

(58) Field of Classification Search
None
See application file for complete search history.

(56) References Cited

U.S. PATENT DOCUMENTS

2014/0213571 A1* 7/2014 Liverton ............. C07D 498/04
                                                        514/210.02

OTHER PUBLICATIONS

A. Bali et al. European Journal of Medicinal Chemistry 74 (2014) 477-490.*
Iwanowicz et al., Bioorg. Med. Chem. Lett., vol. 6, No. 12, pp. 1339-1344 (1996).*
Subedi et al., Synth. Comm., vol. 45, pp. 1704-1709 (2015).*
Subedi et al., Eur. J. Med. Chem., vol. 118 (2016), pp. 208-218.*

* cited by examiner

*Primary Examiner* — Alicia L Otton
(74) *Attorney, Agent, or Firm* — Oblon, McClelland, Maier & Neustadt, L.L.P.

(57) ABSTRACT

Disclosed are 4-substituted-2-(5-substituted-1H-indol-2-yl) phenol derivatives for controlling the proliferation and migration of kinase-overexpressed cells. The phenol derivatives are represented by Formula 1:

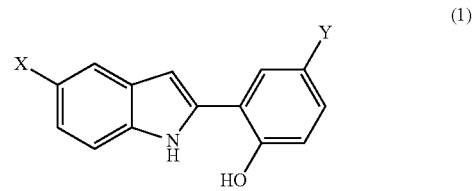

(1)

wherein X is selected from the group consisting of hydrogen, halogen, a cyano group, a trifluoromethyl ($CF_3$) group, an amidine ($C(=NH)NH_2$) group, and a 5-methyl-1,2,4-oxadiazole group, Y is selected from the group consisting of hydrogen, halogen, a phenyl group substituted with one or two substituents selected from the group consisting of halogen, methoxy, nitro, trifluoromethyl, and aminomethyl, CO—R', COOR', OH, O—R', and NH—R', each R' is independently selected from the group consisting of $C_1$-$C_{18}$ alkyl, alkenyl, alkynyl, and —Z-alkyl (wherein Z is a heteroatom selected from the group consisting of O, S, and N or is —$(CH_2)_m$—), and m is an integer from 0 to 5. Also disclosed are methods for preparing the phenol derivatives and pharmaceutical compositions for inhibiting cell proliferation and migration including the phenol derivatives. The phenol derivatives and the pharmaceutical compositions can effectively inhibit the proliferation and migration of kinase-overexpressed cells and can be used for the prevention or treatment of various solid cancers and metastatic cancers.

10 Claims, 4 Drawing Sheets

4-SUBSTITUTED-2-(5-SUBSTITUTED-1H-INDOL-2-YL)PHENOL DERIVATIVES, METHODS FOR PREPARING THE PHENOL DERIVATIVES AND PHARMACEUTICAL COMPOSITIONS FOR INHIBITING CELL PROLIFERATION AND MIGRATION INCLUDING THE PHENOL DERIVATIVES

BACKGROUND OF THE INVENTION

1. Field of the Invention

The present invention relates to 4-substituted-2-(5-substituted-1H-indol-2-yl)phenol derivatives for controlling the proliferation and migration of kinase-overexpressed cells, methods for preparing the phenol derivatives, and pharmaceutical compositions for inhibiting cell proliferation and migration including the phenol derivatives.

2. Description of the Related Art

YANK is an abbreviation for yet another novel kinase and belongs to the AGC family of protein kinases. The group of AGC kinases includes 60 or more protein kinases in the human genome but the exact biological role of genes belonging to the YANK family has not been reported. Previous reports provide some genetic evidence for the association of YANK, a kind of serine/threonine kinase, with human diseases. The YANK1 gene located in chromosome 5q31-q33 was reported to be highly associated with inflammatory diseases. For example, the YANK1 gene was found as one of the YANK1 gene loci associated with Chinese lung cancer patients. In addition, YANK2 was reported to be involved in cancer metastasis and angiogenesis in oral squamous cell carcinoma. Furthermore, YANK3 plays an important role in breast cancer and was reported to be a potential marker for breast cancer.

On the other hand, AT13148 is a multi-AGC kinase inhibitor developed as an oral anticancer agent by Astex Pharmaceuticals and is now being clinically tested. This inhibitor is known to inhibit the phosphorylation of AKT and PKA substrates. However, there have been no reports on drugs or compounds with inhibitory activity against members of the YANK family.

SUMMARY OF THE INVENTION

Thus, the present inventors have made efforts to develop novel compounds that inhibit cell migration and infiltration caused by YANK and to find compounds that inhibit the phosphorylation of YANK3, a member of the YANK family, through in vitro kinase experiments. Therefore, the present invention is intended to provide 4-substituted-2-(5-substituted-1H-indol-2-yl)phenol derivatives that control the proliferation and migration of kinase-overexpressed cells, methods for preparing the phenol derivatives, and pharmaceutical compositions for inhibiting cell proliferation and migration including the phenol derivatives.

One aspect of the present invention provides a compound represented by Formula 1:

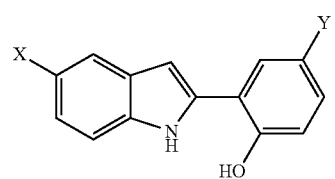

(1)

wherein X is selected from the group consisting of hydrogen, halogen, a cyano group, a trifluoromethyl ($CF_3$) group, an amidine ($C(=NH)NH_2$) group, and a 5-methyl-1,2,4-oxadiazole group, Y is selected from the group consisting of hydrogen, halogen, a phenyl group substituted with one or two substituents selected from the group consisting of halogen, methoxy, nitro, trifluoromethyl, and aminomethyl, CO—R', COOR', OH, O—R', and NH—R', each R' is independently selected from the group consisting of $C_1$-$C_8$ alkyl, alkenyl, alkynyl, and —Z-alkyl (wherein Z is a heteroatom selected from the group consisting of O, S, and N or is —$(CH_2)_m$—), and m is an integer from 0 to 5.

According to one embodiment of the present invention, the compound of Formula 1 may be represented by Formula 2:

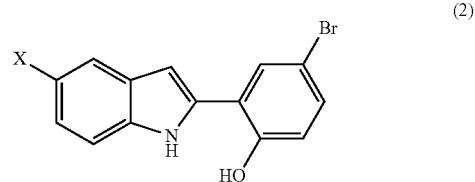

(2)

wherein X is selected from the group consisting of H, F, Cl, CN, and $CF_3$.

According to a further embodiment of the present invention, the compound of Formula 1 may be represented by Formula 3:

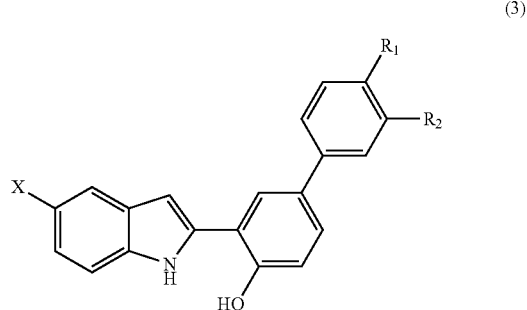

(3)

wherein X is selected from the group consisting of H, F, Cl, CN, and $CF_3$, $R_1$ is selected from the group consisting of H, F, Cl, and $OCH_3$, and $R_2$ is H or $NO_2$.

According to another embodiment of the present invention, the compound of Formula 1 may be represented by Formula 4:

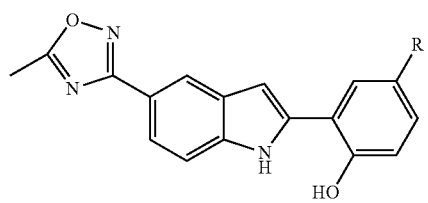

-continued

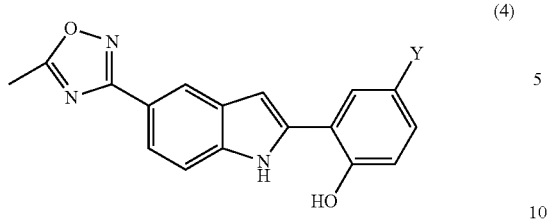

(4)

Y is selected from the group consisting of hydrogen, halogen, a phenyl group substituted with one or two substituents selected from the group consisting of halogen, methoxy, nitro, trifluoromethyl, and aminomethyl, CO—R', COOR', OH, O—R', and NH—R', each R' is independently selected from the group consisting of $C_1$-$C_{18}$ alkyl, alkenyl, alkynyl, and —Z-alkyl (wherein Z is a heteroatom selected from the group consisting of O, S, and N or is —$(CH_2)_m$—), and m is an integer from 0 to 5.

According to another embodiment of the present invention, the compound of Formula 1 may be represented by Formula 5:

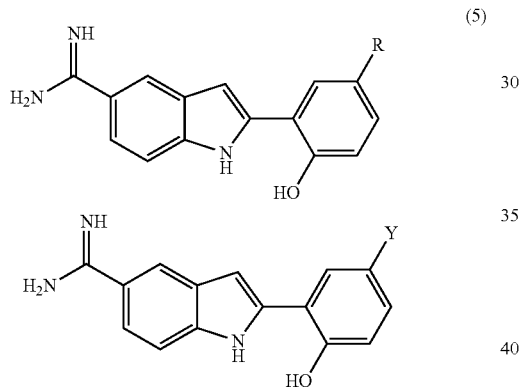

(5)

wherein Y is selected from the group consisting of hydrogen, halogen, a phenyl group substituted with one or two substituents selected from the group consisting of halogen, methoxy, nitro, trifluoromethyl, and aminomethyl, CO—R', COOR', OH, O—R', and NH—R', each R' is independently selected from the group consisting of $C_1$-$C_{18}$ alkyl, alkenyl, alkynyl, and —Z-alkyl (wherein Z is a heteroatom selected from the group consisting of O, S, and N or is —$(CH_2)_m$—), and m is an integer from 0 to 5.

According to yet another embodiment of the present invention, the compound of Formula 1 may be any one of the compounds represented by Formulae 6 to 37:

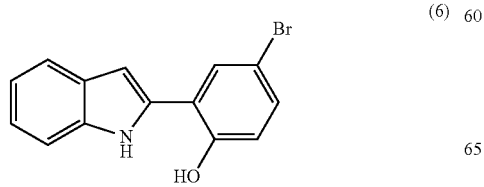

(6)

(7)

(8)

(9)

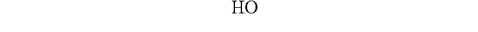

(10)

(11)

(12)

(13)

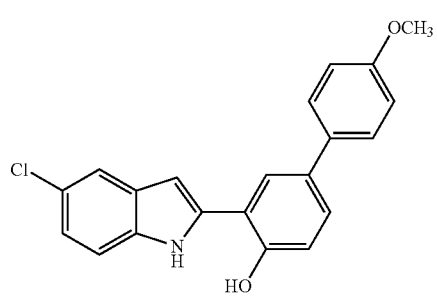
(14)
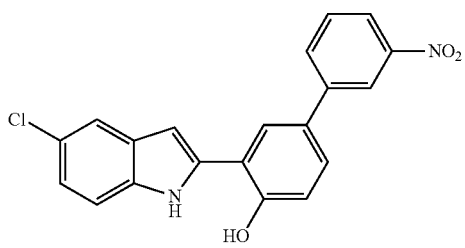
(15)
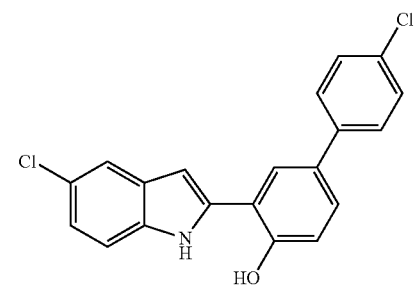
(16)
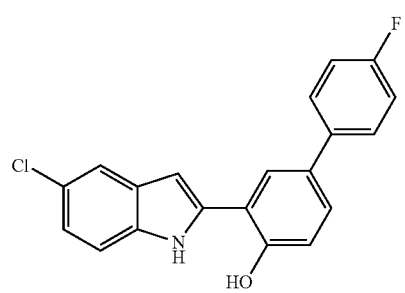
(17)
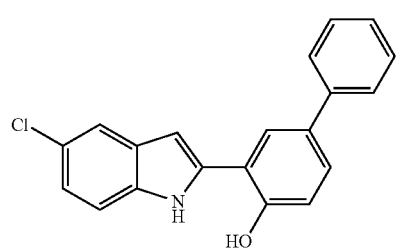
(18)
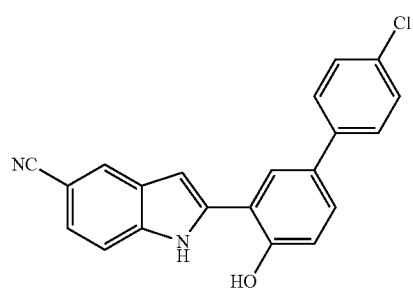
(19)
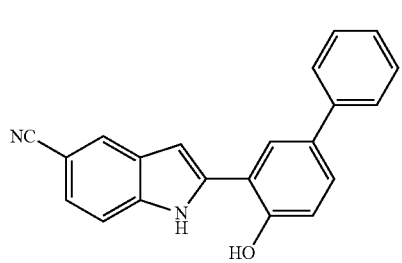
(20)
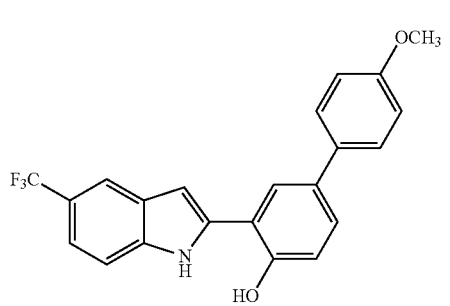
(21)
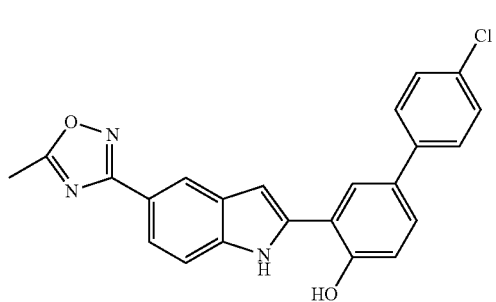
(22)
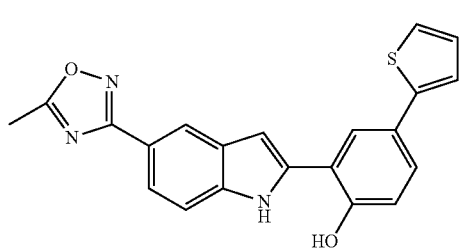
(23)
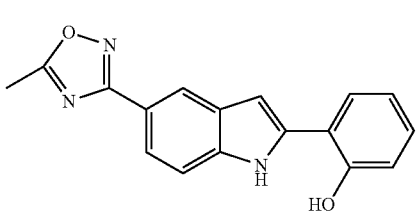
(24)
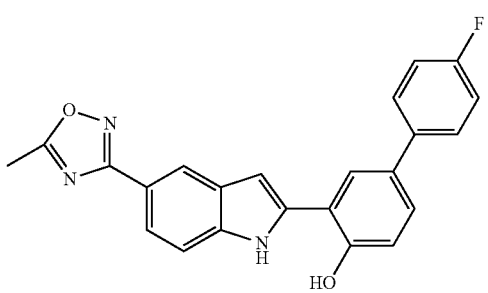
(25)

(26)
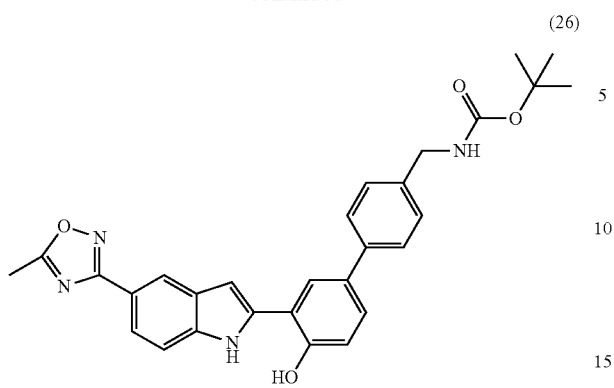
(27)
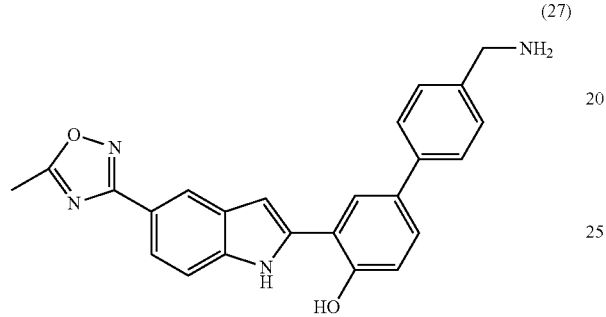
(28)
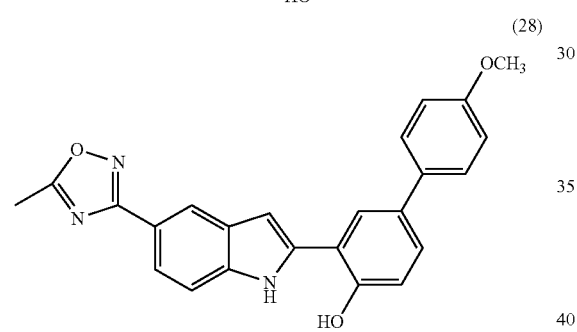
(29)
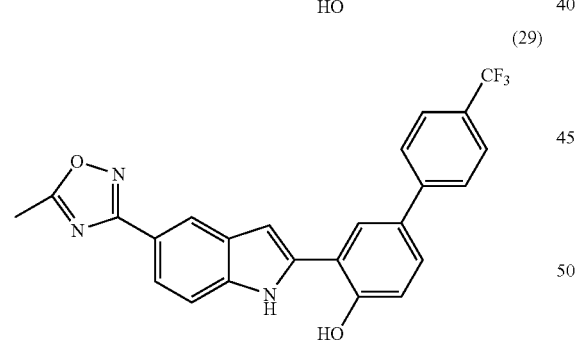
(30)
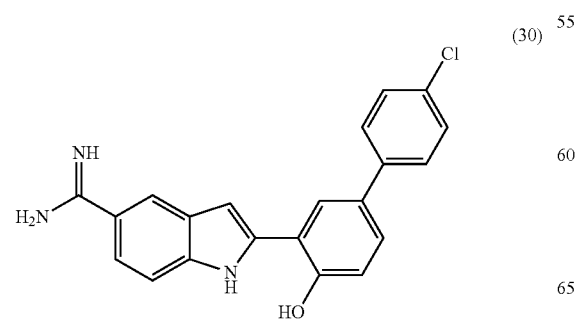
(31)
(32)
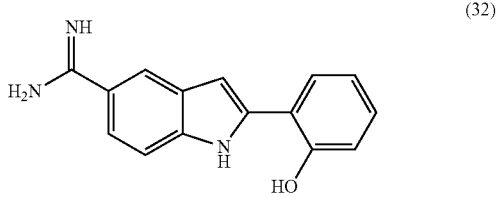
(33)
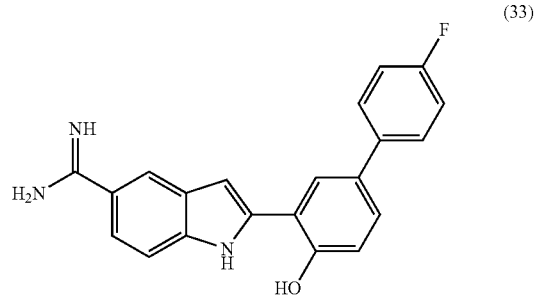
(34)
(35)
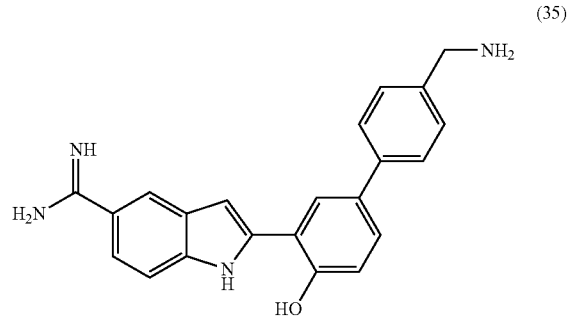

-continued

(36)
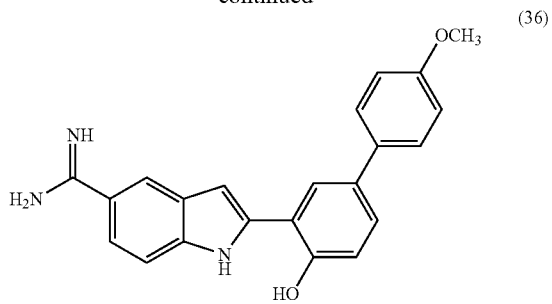

(37)
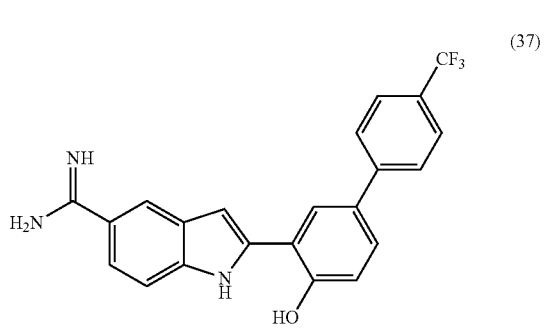 [SMILES: N=C(N)c1ccc2[nH]c(-c3cc(-c4ccc(C(F)(F)F)cc4)ccc3O)cc2c1]

The present invention also provides a method for preparing a compound represented by Formula 1:

(1)
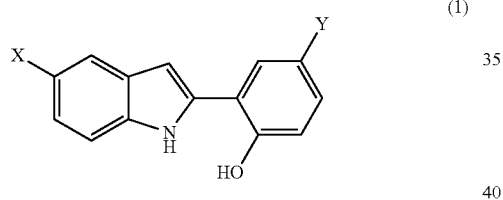

wherein X is selected from the group consisting of hydrogen, halogen, a cyano group, and a trifluoromethyl (CF$_3$) group, Y is selected from the group consisting of hydrogen, halogen, a phenyl group substituted with one or two substituents selected from the group consisting of halogen, methoxy, nitro, trifluoromethyl, and aminomethyl, CO—R', COOR', OH, O—R', and NH—R', each R' is independently selected from the group consisting of C$_1$-C$_{18}$ alkyl, alkenyl, alkynyl, and —Z-alkyl (wherein Z is a heteroatom selected from the group consisting of O, S, and N or is —(CH$_2$)$_m$—), and m is an integer from 0 to 5, the method including reacting a compound of Formula 38:

(38)

wherein X is as defined in Formula 1, with the compound of Formula 39:

(39)
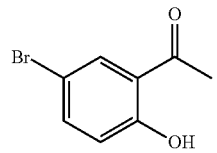

in a solution including piperidine and toluene to prepare a compound of Formula 40:

(40)
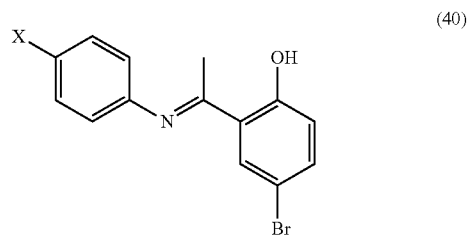

wherein X is as defined in Formula 1, and reacting the compound of Formula 40 with tetrabutylammonium bromide.

According to one embodiment of the present invention, the method may further include reacting the compound of Formula 1 with a compound of Formula 41:

(41)
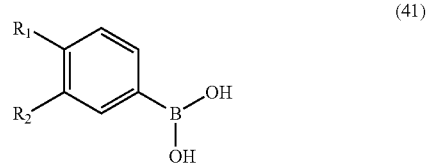

wherein R$_1$ and R$_2$ are each independently selected from the group consisting of H, OCH$_3$, Cl, F, and NO$_2$, to prepare a compound of Formula 42:

(42)
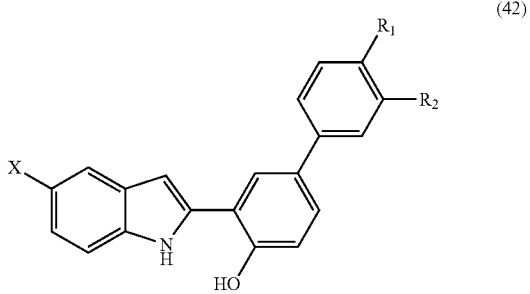

wherein X is selected from the group consisting of hydrogen, halogen, a cyano group, and a trifluoromethyl (CF$_3$) group and R$_1$ and R$_2$ are as defined in Formula 41.

The present invention also provides a method for preparing a compound represented by Formula 1:

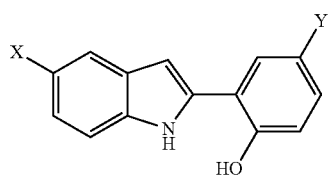

(1)

wherein X is an amidine (C(=NH)NH$_2$) or 5-methyl-1,2,4-oxadiazole group, Y is selected from the group consisting of hydrogen, halogen, a phenyl group substituted with one or two substituents selected from the group consisting of halogen, methoxy, nitro, trifluoromethyl, and aminomethyl, CO—R', COOR', OH, O—R', and NH—R', each R' is independently selected from the group consisting of C$_1$-C$_{18}$ alkyl, alkenyl, alkynyl, and —Z-alkyl (wherein Z is a heteroatom selected from the group consisting of 0, S, and N or is —(CH$_2$)$_m$—), and m is an integer from 0 to 5, the method including reacting the compound of Formula 43:

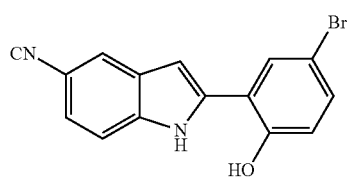

(43)

with NH$_2$OH.HCl, Na$_2$CO$_3$, and ethanol to prepare the compound of Formula 44:

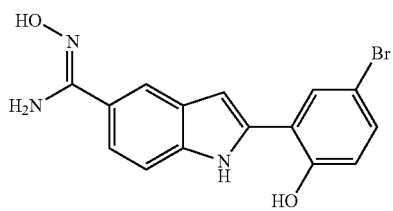

(44)

reacting the compound of Formula 44 with NaOCH$_2$CH$_3$, ethanol, and ethyl acetate to prepare the compound of Formula 45:

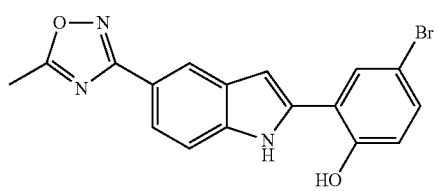

(45)

reacting the compound of Formula 45 with a compound of Formula 46:

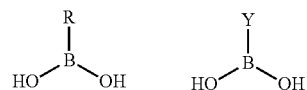

(46)

wherein Y is selected from the group consisting of hydrogen, halogen, a phenyl group substituted with one or two substituents selected from the group consisting of halogen, methoxy, nitro, trifluoromethyl, and aminomethyl, CO—R', COOR', OH, O—R', and NH—R', each R' is independently selected from the group consisting of C$_1$-C$_{18}$ alkyl, alkenyl, alkynyl, and —Z-alkyl (wherein Z is a heteroatom selected from the group consisting of O, S, and N or is —(Cl)$_m$—), and m is an integer from 0 to 5, to prepare a compound of Formula 47.

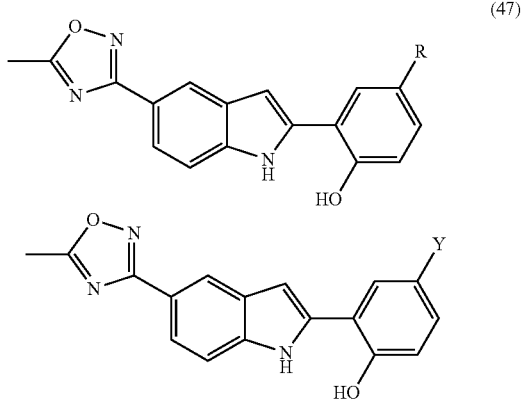

(47)

wherein Y is as defined in Formula 46, and
reducing the compound of Formula 47.

The present invention also provides a pharmaceutical composition for inhibiting cell proliferation and migration including the compound of Formula 1 or a pharmaceutically acceptable salt thereof as an active ingredient.

According to one embodiment of the present invention, the pharmaceutical composition may have prophylactic and therapeutic efficacy against cancer.

According to a further embodiment of the present invention, the pharmaceutical composition may further include one or more ingredients selected from the group consisting of prophylactic and therapeutic agents for cancer diseases, excipients, diluents, adjuvants, and stabilizers.

According to another embodiment of the present invention, the stabilizers may be selected from the group consisting of proteins, carbohydrates, buffers, and mixtures thereof.

The phenol derivatives and the pharmaceutical compositions of the present invention can effectively inhibit the proliferation and migration of kinase-overexpressed cells and can be used for the prevention or treatment of various solid cancers and metastatic cancers.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

The present invention will now be described in more detail.

The present inventors have found for the first time that phenol derivatives having a structure of Formula 1 are effective in inhibiting the proliferation and migration of kinase-overexpressed cells. The present invention has been accomplished based on this finding.

Thus, the present invention provides phenol derivatives represented by Formula

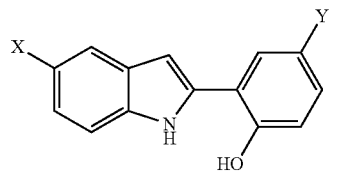

(1)

wherein X is selected from the group consisting of hydrogen, halogen, a cyano group, a trifluoromethyl ($CF_3$) group, an amidine ($C(=NH)NH_2$) group, and a 5-methyl-1,2,4-oxadiazole group, Y is selected from the group consisting of hydrogen, halogen, a phenyl group substituted with one or two substituents selected from the group consisting of halogen, methoxy, nitro, trifluoromethyl, and aminomethyl, CO—R', COOR', OH, O—R', and NH—R', each R' is independently selected from the group consisting of $C_1$-$C_{18}$ alkyl, alkenyl, alkynyl, and —Z-alkyl (wherein Z is a heteroatom selected from the group consisting of O, S, and N or is —($CH_2$)$_m$—), and m is an integer from 0 to 5.

The phenol derivatives represented by Formula 1 include both indole and phenol moieties in common. The phenol derivatives may be optionally substituted with other substituents at the 5-position of the indole ring and at the 4-position of the phenol ring.

For example, the phenol derivatives of Formula 1 may belong to any one of the four groups of compounds represented by Formulae 2 to 5:

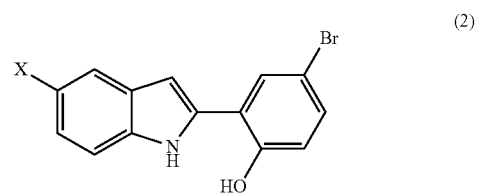

(2)

wherein X is selected from the group consisting of H, F, Cl, CN, and $CF_3$;

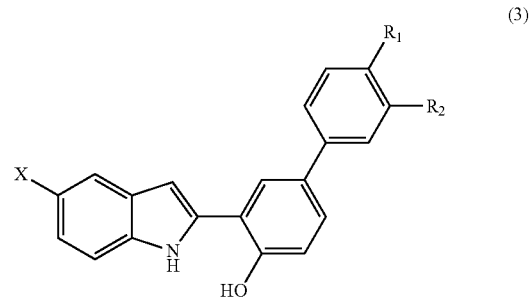

(3)

wherein X is selected from the group consisting of H, F, Cl, CN, and $CF_3$, $R_1$ is selected from the group consisting of H, F, Cl, and $OCH_3$, and $R_2$ is H or $NO_2$;

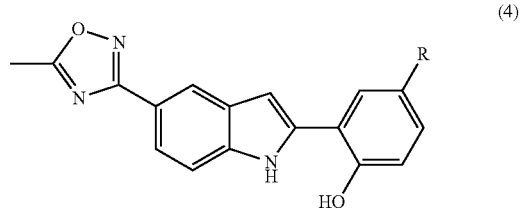

(4)

wherein R is selected from the group consisting of H, phenyl, 2-thiophene, 4-Cl-phenyl, 4-F-phenyl, 4-$CH_2$NHBoc-phenyl, 4-$OCH_3$-phenyl, and 4-$CF_3$-phenyl; and

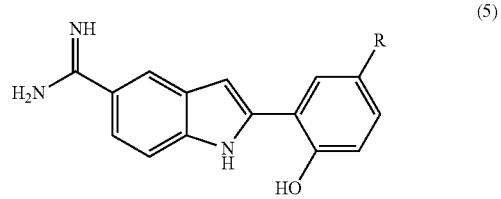

(5)

wherein R is selected from the group consisting of H, phenyl, 2-thiophene, 4-Cl-phenyl, 4-F-phenyl, 4-$CH_2$NHBoc-phenyl, 4-$CH_2NH_2$-phenyl, 4-$OCH_3$-phenyl, and 4-$CF_3$-phenyl.

Specifically, the phenol derivatives of Formula 1 may be the compounds represented by Formulae 6 to 37:

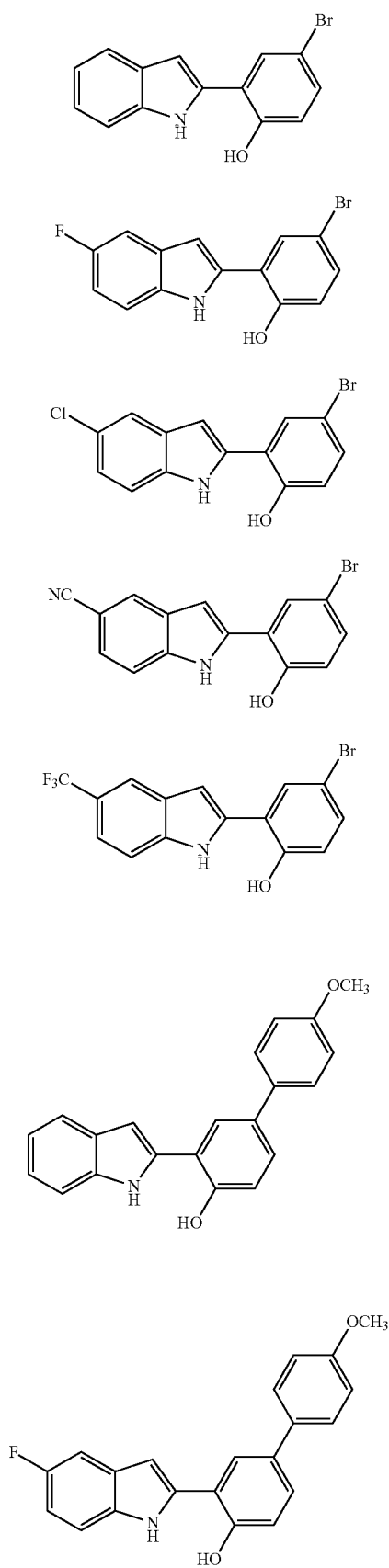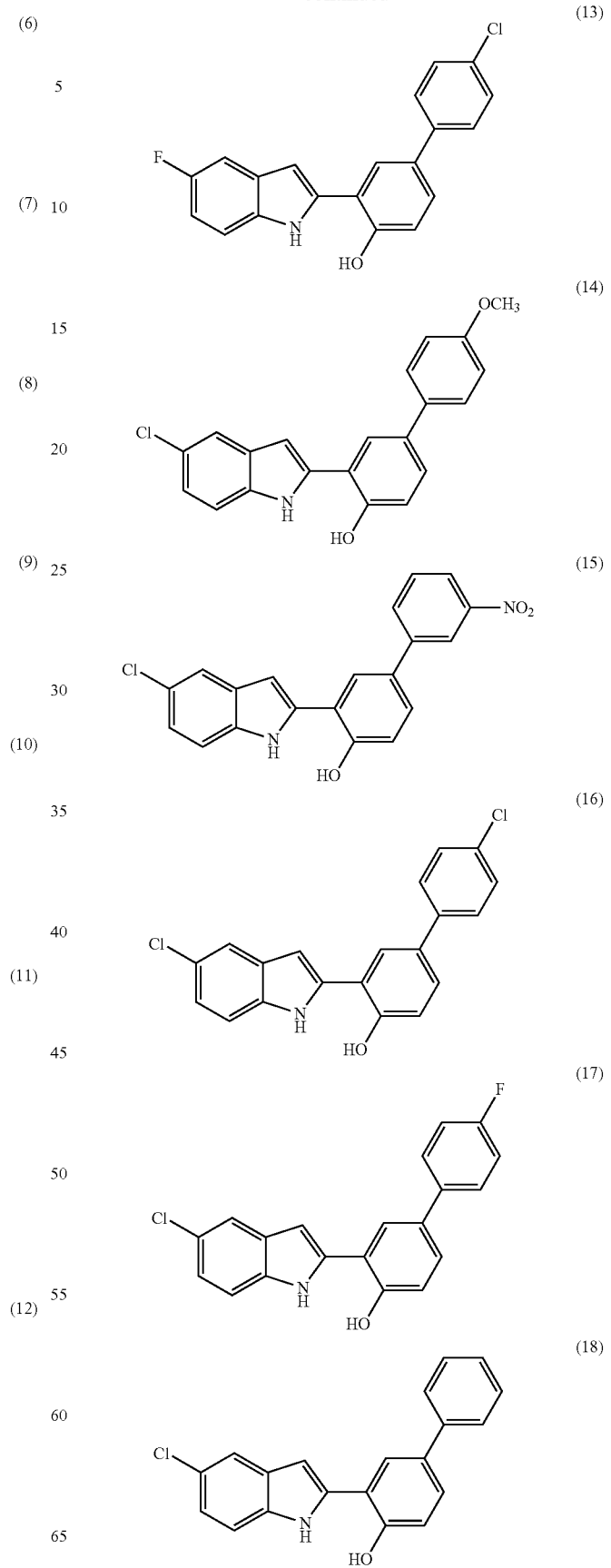

-continued
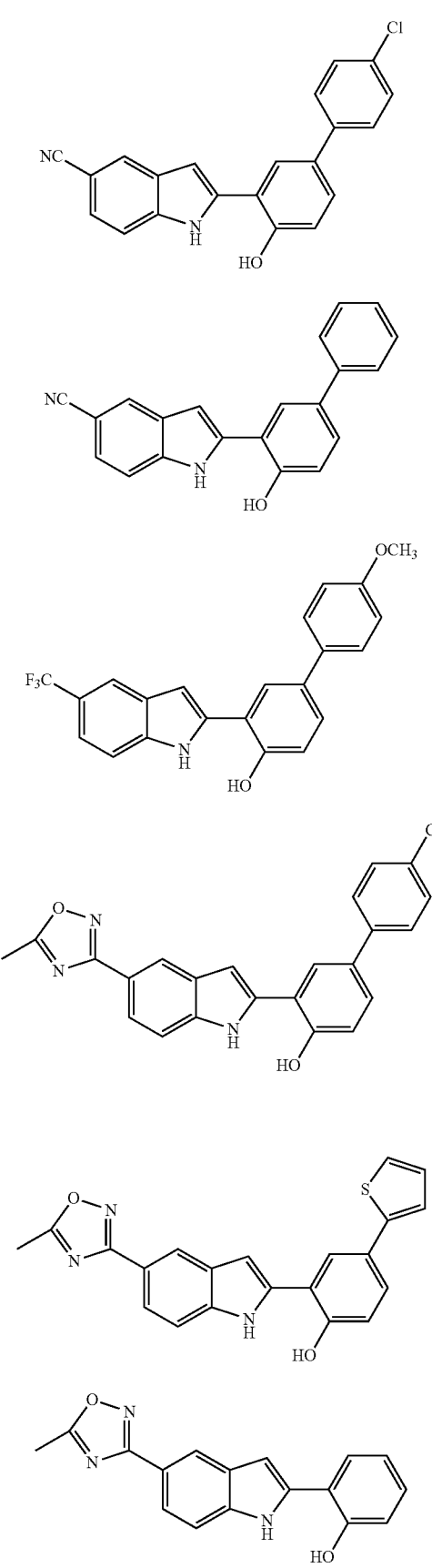
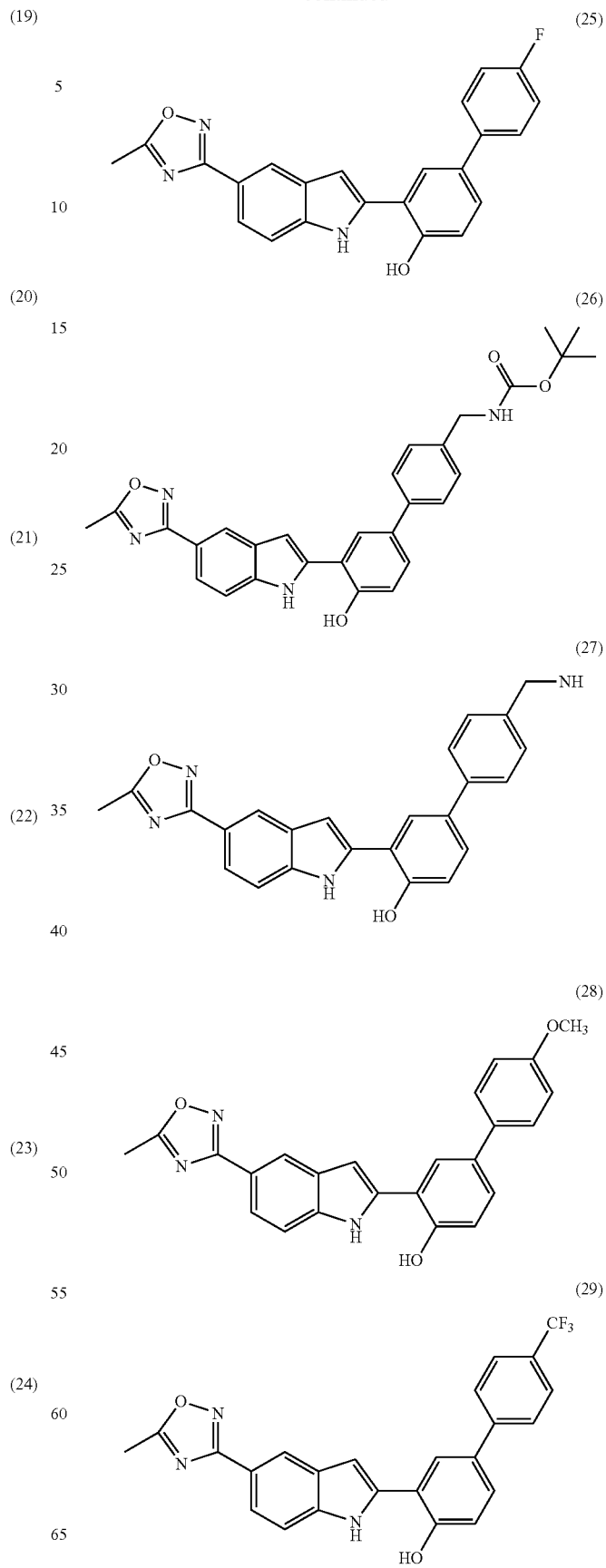

-continued

(30)
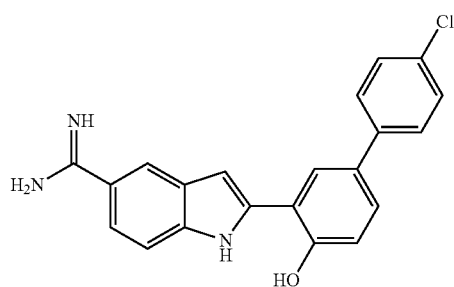

(31)
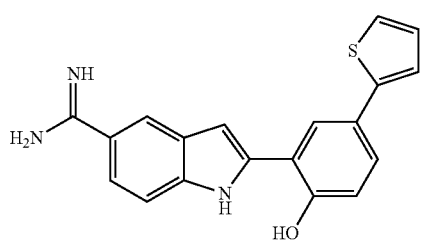

(32)
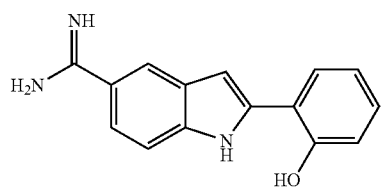

(33)
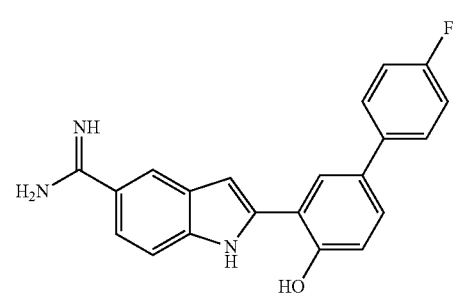

(34)
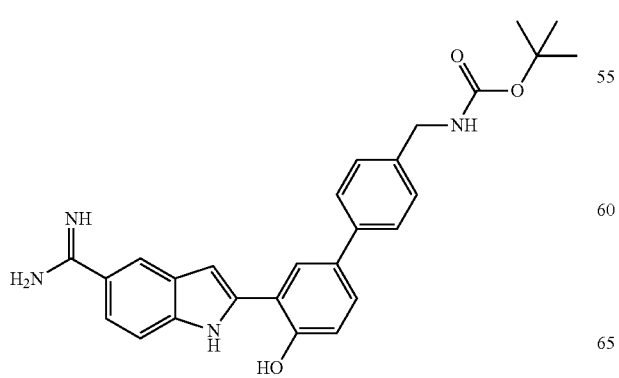

-continued

(35)
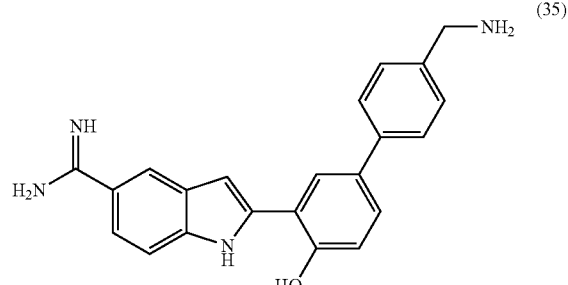

(36)
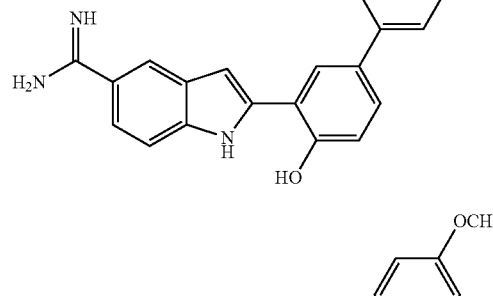

(37)
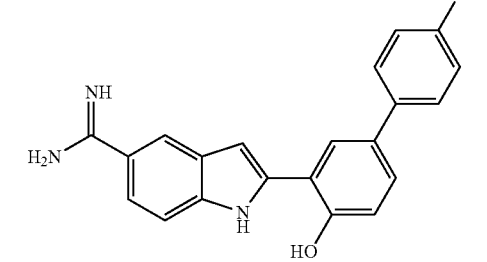

The phenol derivatives of the present invention may be prepared through imine formation, palladium-catalyzed indole cyclization, and Suzuki coupling. For example, the phenol derivatives may be prepared by Suzuki coupling of imines and substituted phenylboronic acids. The imines may be synthesized from 4-substituted anilines and 5-bromo-2-hydroxyacetophenone as starting materials.

Figure 1:
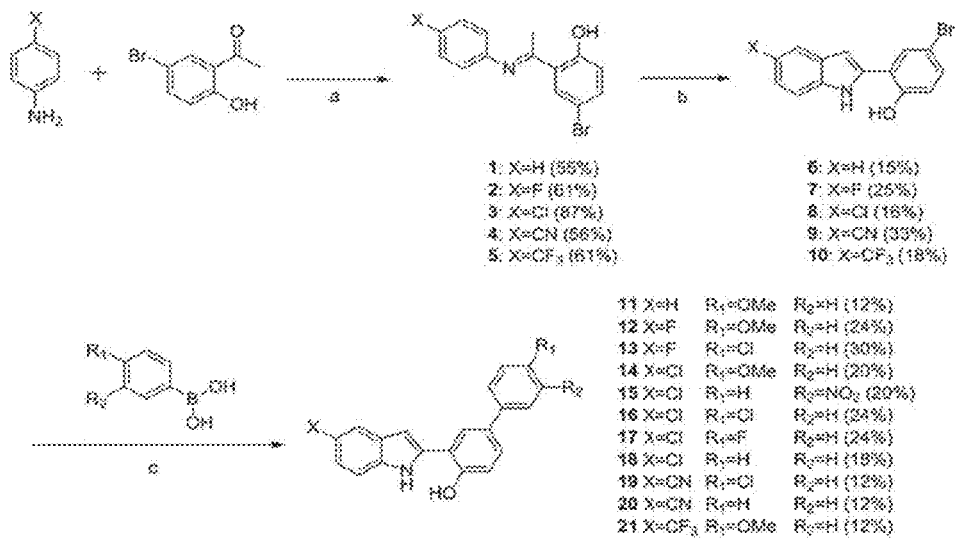
FIG. 1 is a schematic reaction scheme for the synthesis of phenol derivatives substituted with a F, Cl, CN or CF$_3$ group at the 5-position of indole.
Figure 2:
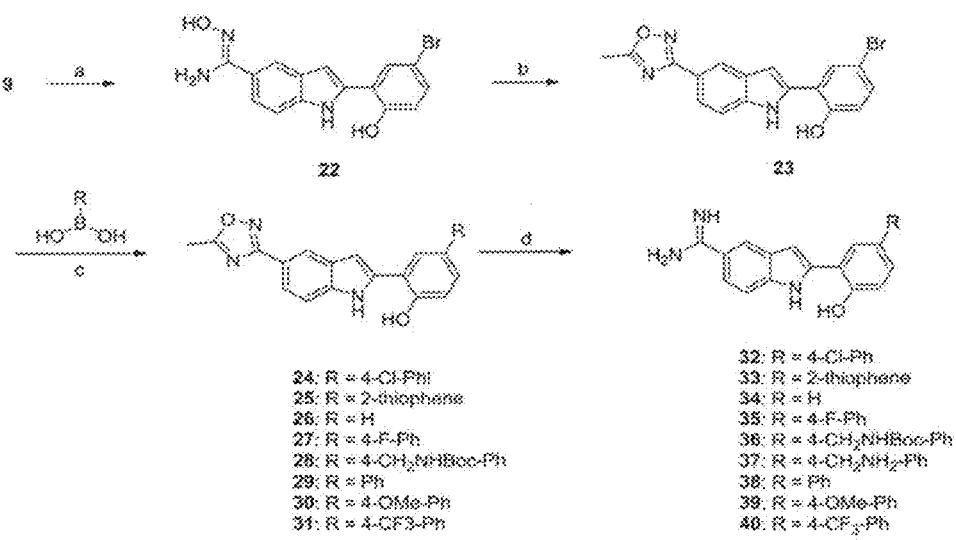
FIG. 2 is a schematic reaction scheme for the synthesis of phenol derivatives substituted with an oxadiazole ring or an amidine group at the 5-position of indole.
Figure 3:
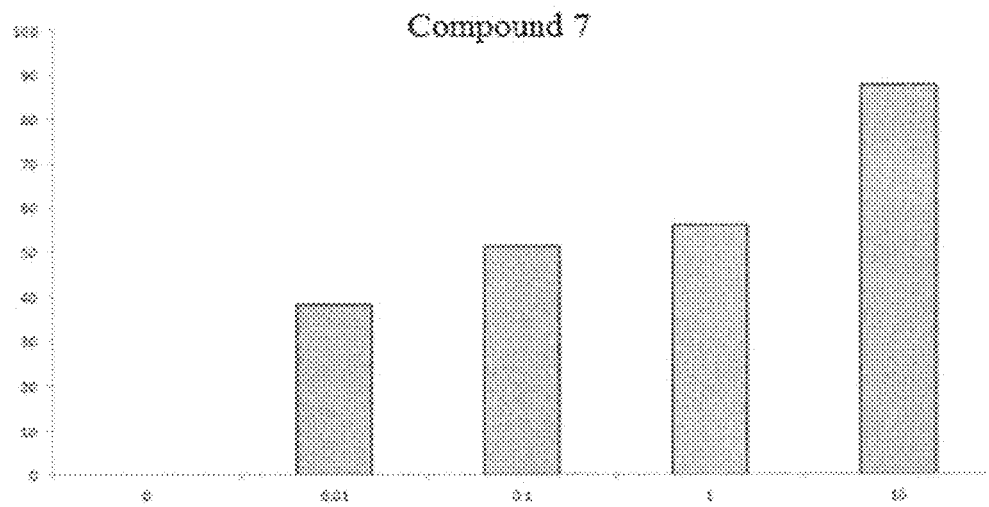
FIG. 3 shows concentration-dependent inhibitions of proliferation of YANK-expressed cells by treatment with the phenol derivative of Formula 7.
Figure 4:
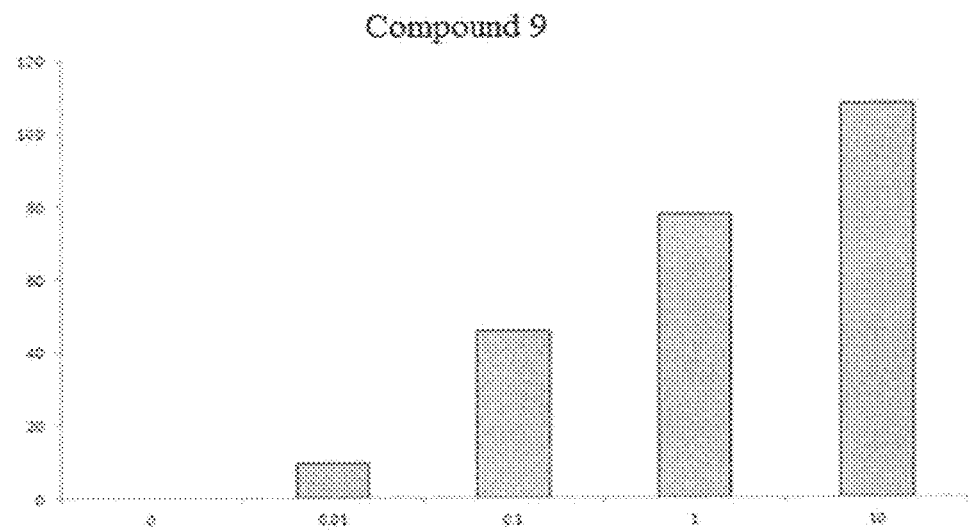
FIG. 4 shows concentration-dependent inhibitions of proliferation of YANK-expressed cells by treatment with the phenol derivative of Formula 9.
Figure 5:
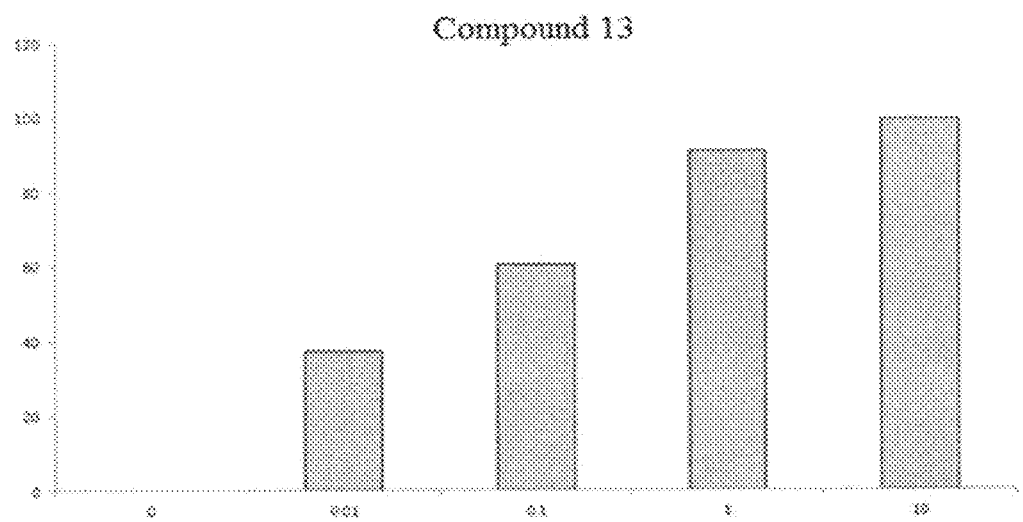
FIG. 5 shows concentration-dependent inhibitions of proliferation of YANK-expressed cells by treatment with the phenol derivative of Formula 13.
Figure 6:
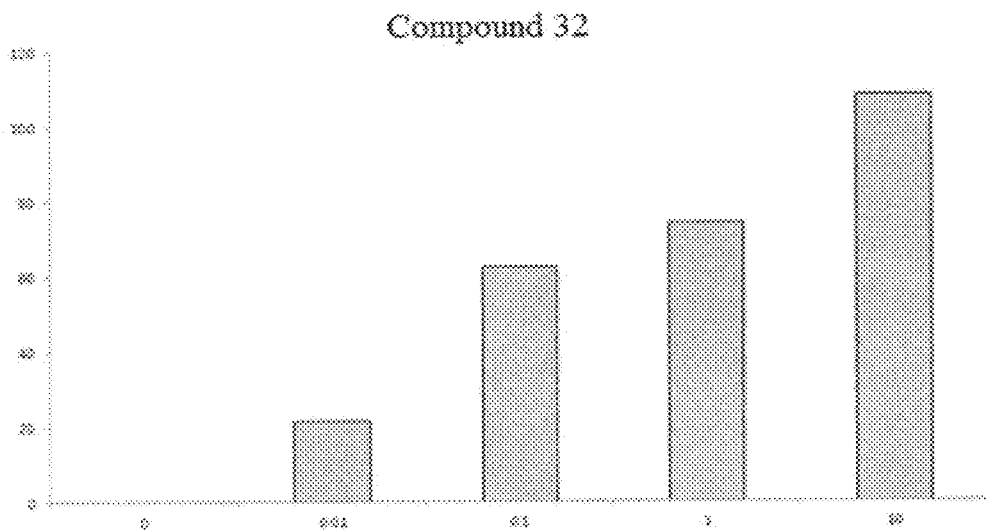
FIG. 6 shows concentration-dependent inhibitions of proliferation of YANK-expressed cells by treatment with the phenol derivative of Formula 32.

For example, reaction schemes for the synthesis of phenol derivatives substituted with a F, Cl, CN or $CF_3$ group at the 5-position of the indole ring and phenol derivatives substituted with an oxadiazole ring or an amidine group at the 5-position of the indole ring are schematically shown in FIGS. 1 and 2, respectively.

Thus, the present invention provides a method for preparing phenol derivatives substituted with a F, Cl, CN or $CF_3$ group at the 5-position of indole, represented by Formula 1:

(1)
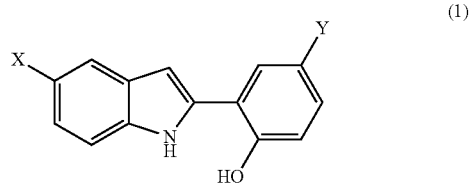

wherein X is selected from the group consisting of hydrogen, halogen, a cyano group, and a trifluoromethyl ($CF_3$) group, Y is selected from the group consisting of hydrogen, halogen, a phenyl group substituted with one or two substituents selected from the group consisting of halogen, methoxy, nitro, trifluoromethyl, and aminomethyl, CO—R', COOR', OH, O—R', and NH—R', each R' is independently selected from the group consisting of $C_1$-$C_{18}$ alkyl, alkenyl, alkynyl, and —Z-alkyl (wherein Z is a heteroatom selected from the group consisting of O, S, and N or is —$(CH_2)_m$—), and m is an integer from 0 to 5, the method including reacting a compound of Formula 38:

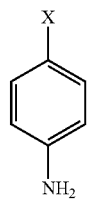

(38)

wherein X is as defined in Formula 1, with the compound of Formula 39:

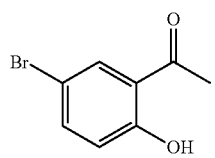

(39)

in a solution including piperidine and toluene to prepare a compound of Formula 40:

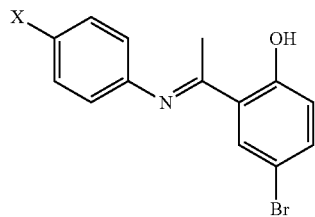

(40)

wherein X is as defined in Formula 1, and reacting the compound of Formula 40 with tetrabutylammonium bromide.

The phenol derivatives of Formula 1 may further react with a compound of Formula 41:

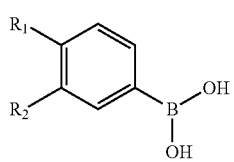

(41)

wherein $R_1$ and $R_2$ are each independently selected from the group consisting of H, $OCH_3$, Cl, F, and $NO_2$, to prepare a compound of Formula 42:

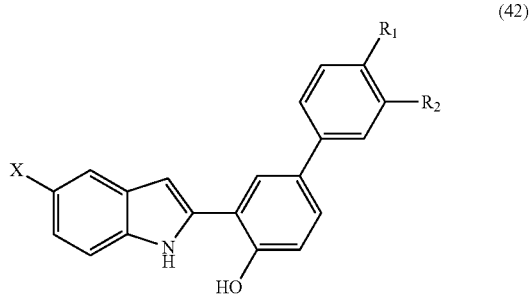

(42)

wherein X is selected from the group consisting of hydrogen, halogen, a cyano group, and a trifluoromethyl ($CF_3$) group and $R_1$ and $R_2$ are as defined in Formula 41.

The present invention also provides a method for preparing phenol derivatives substituted with an oxadiazole ring or an amidine group at the 5-position of indole, represented by Formula 1:

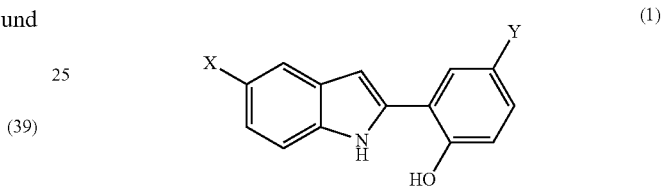

(1)

wherein X is an amidine (C(=NH)$NH_2$) or 5-methyl-1,2,4-oxadiazole group, Y is selected from the group consisting of hydrogen, halogen, a phenyl group substituted with one or two substituents selected from the group consisting of halogen, methoxy, nitro, trifluoromethyl, and aminomethyl, CO—R', COOR', OH, O—R', and NH—R', each R' is independently selected from the group consisting of $C_1$-$C_{18}$ alkyl, alkenyl, alkynyl, and —Z-alkyl (wherein Z is a heteroatom selected from the group consisting of O, S, and N or is —$(CH_2)_m$—), and m is an integer from 0 to 5, the method including reacting the compound of Formula 43:

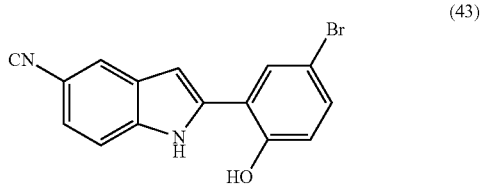

(43)

with $NH_2OH \cdot HCl$, $Na_2CO_3$, and ethanol to prepare the compound of Formula 44:

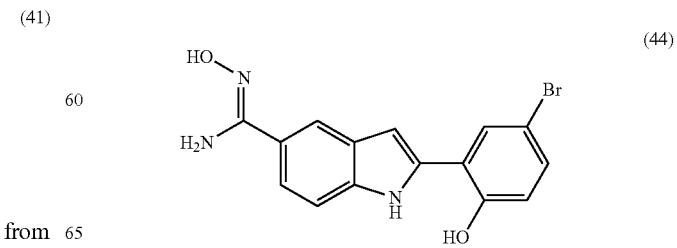

(44)

reacting the compound of Formula 44 with NaOCH$_2$CH$_3$, ethanol, and ethyl acetate to prepare the compound of Formula 45:

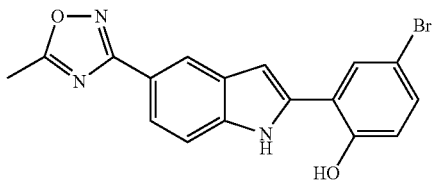

(45)

reacting the compound of Formula 45 with a compound of Formula 46.

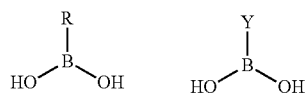

(46)

wherein Y is selected from the group consisting of hydrogen, halogen, a phenyl group substituted with one or two substituents selected from the group consisting of halogen, methoxy, nitro, trifluoromethyl, and aminomethyl, CO—R', COOR', OH, O—R', and NH—R', each R' is independently selected from the group consisting of C$_1$-C$_{18}$ alkyl, alkenyl, alkynyl, and —Z-alkyl (wherein Z is a heteroatom selected from the group consisting of O, S, and N or is —(Cl)$_m$—), and m is an integer from 0 to 5, to prepare a compound of Formula 47.

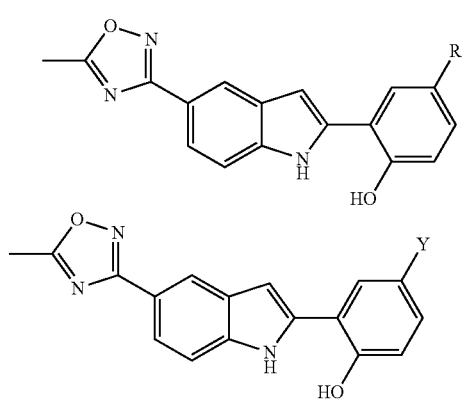

(47)

wherein Y is as defined in Formula 46, and
reducing the compound of Formula 47.

The phenol derivatives of Formula 1 according to the present invention and their pharmaceutically acceptable salts exhibit outstanding inhibitory activities on cell proliferation and migration, as can be seen from the Examples section that follows.

Thus, the present invention provides pharmaceutical compositions for inhibiting cell proliferation and migration including at least one of the phenol derivatives of Formula 1 or their pharmaceutically acceptable salts as an active ingredient.

The term "including ~ as an active ingredient" as used herein means the presence of the corresponding ingredient in an amount necessary or sufficient to achieve the desired biological effects. In real applications, the active ingredient is used in a therapeutically effective amount to treat a target disease and such an amount can suitably be determined taking into consideration other toxicities caused by the active ingredient. For example, the amount of the active ingredient may vary depending on various factors, such as the disease or condition to be treated, the dosage form of each composition, the size of a subject or the severity of the disease or condition. The effective amount of each composition can be empirically determined by those skilled in the art without excessive experiments.

Therefore, the compositions of the present invention are useful as prophylactic or therapeutic agents for cancer. The compositions of the present invention may be complexed with other prophylactic and therapeutic drugs before administration or may further include one or more ingredients selected from the group consisting of excipients, diluents, adjuvants, and stabilizers.

The dosage forms of the compositions according to the present invention may vary depending on the mode of administration. Examples of such dosage forms include, but are not limited to, solid, semi-solid, and liquid formulations, such as tablets, pills, powders, capsules, gels, ointments, emulsions, and suspensions. The compositions of the present invention may be administered in unit dosage forms suitable for single administration of precise doses. Depending on desired formulations, the compositions may include one or more pharmaceutically acceptable excipients, diluents, adjuvants, and stabilizers, which are generally used in the preparation of formulations for human administration. The excipients refer to ingredients defined as aqueous carriers. As the diluents, there may be mentioned, for example, distilled water, physiological saline, Ringer's solution, glucose solution, and Hank's solution. The pharmaceutical compositions of the present invention may also be administered in the form of complexes with other drug preparations or pharmaceutical preparations for the prevention and treatment of cancer diseases. Various kinds of prophylactic and therapeutic drugs for cancer can be taken into consideration by those skilled in the art. Such additional ingredients as excipients, diluents, adjuvant, and stabilizers may be used in amounts effective to acquire pharmaceutically acceptable formulations in view of the solubility, biological activity, and other characteristics of the active ingredient. The stabilizers may be selected from the group consisting of proteins, carbohydrates, buffers, and mixtures thereof.

The present invention will be explained in more detail with reference to the following examples. However, these examples are provided to assist in understanding the invention and are not intended to limit the scope of the invention.

Example 1: Synthesis of Biphenyl Indole Derivatives

Phenol derivatives were prepared by the following procedures, which can be understood with reference to FIGS. 1 and 2. The following compound numbers may be different from the foregoing compound numbers.

General Procedure for the Synthesis of Imine Intermediates

Piperidine (1 mL) was slowly added to a solution of 4-substituted aniline (10.7 mmol) and 5-bromo-20-hydroxyacetophenone (10.7 mmol) in toluene (10 mL). The mixture equipped with the Dean-Stark apparatus was allowed to stir at 130° C. for about 6 h. The reaction mixture was cooled to room temperature and the excess solvent was removed under reduced pressure. The resulting residue was washed with a mixture of hexane and ethyl acetate to provide the corresponding imines.

(E)-4-Bromo-2-(1-(phenylimino)ethyl)phenol (1)

Yield: 55%, $R_f$: 0.6 (hexane/ethyl acetate=6/1), $^1$H NMR (300 MHz, DMSO-$d_6$): δ 14.72 (s, 1H, NH), 7.90 (d, 1H, Ar—H, J=2.4 Hz), 7.55 (dd, 1H, Ar—H, J=2.4 Hz & 8.7 Hz), 7.45 (t, 2H, Ar—H, J=7.5 Hz), 7.24 (t, 1H, Ar—H, J=7.2 Hz), 7.50-6.90 (m, 2H, Ar—H), 6.25 (d, 1H, Ar—H, J=8.7 Hz), 2.34 (s, 3H, CH$_3$), ESI-MS: [M–H]$^-$ calcd for $C_{14}H_{12}BrNO$: 288.0, found: 288.0.

(E)-4-Bromo-2-(1-(4-fluorophenylimino)ethyl)phenol (2)

Yield: 61%, $R_f$: 0.51 (hexane/ethyl acetate=9/1), $^1$H NMR (300 MHz, CDCl$_3$): δ 14.61 (s, 1H, NH), 7.73 (d, 1H, Ar—H, J=2.4 Hz), 7.45 (dd, 1H, Ar—H, J=2.4 & 8.7 Hz), 7.16-7.06 (m, 2H, Ar—H), 6.95-6.85 (m, 3H, Ar—H), 2.34 (s, 3H, CH$_3$), ESI-MS: [M+H]$^+$ calcd for $C_{14}H_{11}BrFNO$: 308.0, found: 308.0.

(E)-4-Bromo-2-(1-(4-chlorophenylimino)ethyl)phenol (3)

Yield: 87%, $R_f$: 0.38 (hexane/ethyl acetate=8/1), $^1$H NMR (300 MHz, CDCl$_3$): δ 7.73 (d, 1H, Ar—H, J=2.4 Hz), 7.47 (dd, 1H, Ar—H, J=2.4 Hz & 9.0 Hz), 7.39 (d, 2H, Ar—H, J=8.7 Hz), 6.93 (d, 1H, Ar—H, J=2.4 Hz), 6.86 (d, 1H, Ar—H, J=8.4 Hz) 2.34 (s, 3H, CH$_3$), ESI-MS: [M+H]$^+$ calcd for $C_{14}H_{11}BrClNO$: 326.0, found: 325.9.

(E)-4-((1-(5-Bromo-2-hydroxyphenyl)ethylidene)amino)benzonitrile (4)

Yield: 56%, $R_f$: 0.52 (hexane/ethyl acetate=9/1), $^1$H NMR (300 MHz, CDCl$_3$): δ 13.70 (s, 1H, NH), 7.78-7.70 (m, 3H, Ar—H), 7.50 (dd, 1H, Ar—H, J=2.4 & 8.7 Hz), 7.02 (d, 2H, Ar—H, J=8.7 Hz), 6.95 (d, 2H, Ar—H, J=9.0 Hz), 2.34 (s, 3H, CH$_3$), ESI-MS: [M–H]$^-$ calcd for $C_{15}H_{11}BrN_2O$: 315.0034, found: 314.9775.

(E)-4-Bromo-2-(1-(4-(trifluoromethyl)phenylimino)ethyl)phenol (5)

Yield: 61%, $R_f$: 0.42 (hexane/ethyl acetate=9/1), $^1$H NMR (300 MHz, CDCl$_3$): δ 14.02 (s, 1H, NH), 7.74 (d, 1H, Ar—H, J=2.4 Hz), 7.67 (d, 2H, Ar—H, J=8.1 Hz), 7.49-7.13 (m, 1H, Ar—H), 7.00 (d, 2H, Ar—H, J=8.1 Hz), 6.93 (dd, 1H, Ar—H, J=2.1 & 8.7 Hz), 2.32 (s, 3H, CH$_3$), ESI-MS: [M+H]$^+$ calcd for $C_{15}H_{11}BrF_3NO$: 358.0, found: 357.9.

General Procedure for the Synthesis of Indole Intermediates

Pd(OAc)$_2$ (156 mg, 0.68 mmol), Bu$_4$NBr (2.22 g, 6.88 mmol), and 5-bromo-2-hydroxyacetophenone (10.7 mmol) were added to a solution of imine intermediates (3.44 mmol) in DMSO (10 mL). The mixture was allowed to stir at 110° C. for about 12 h. Upon cooling to room temperature, the reaction mixture was diluted with water (50 mL) and ethyl acetate (50 mL). The combined organic layer was dried over MgSO$_4$, filtered, and concentrated under reduced pressure. The crude residue was purified by column chromatography to afford the corresponding indole compounds.

4-Bromo-2-(1H-indol-2-yl)phenol (6)

Yield: 15%, $R_f$: 0.28 (hexane/ethyl acetate=4/1), $^1$H NMR (300 MHz, CDCl$_3$): δ 9.20 (s, 1H, NH), 7.78 (d, 1H, Ar—H, J=2.4 Hz), 7.64 (d, 1H, Ar—H, J=7.8 Hz), 7.41 (d, 1H, Ar—H, J=8.1 Hz), 7.29-7.09 (m, 3H, Ar—H), 6.85 (d, 1H, Ar—H, J=6.8 Hz), 6.79 (d, 1H, Ar—H, J=1.5 Hz), 5.86 (s, 1H, OH), ESI-MS: [M–H]$^-$ calcd for $C_{14}H_9BrClNO$: 286.0, found: 286.0.

4-Bromo-2-(5-fluoro-1H-indol-2-yl)phenol (7)

Yield: 25%, $R_f$=0.32 (hexane/ethyl acetate=3/2), $^1$H NMR (300 MHz, DMSO-$d_6$): δ 11.36 (s, 1H, NH), 10.53 (s, 1H, OH), 7.92 (d, 1H, Ar—H, J=2.4 Hz), 7.45 (dd, 1H, Ar—H, J=4.8 & 8.7 Hz), 7.33-7.25 (m, 2H, Ar—H), 7.07 (s, 1H, Ar—H), 6.98-6.85 (m, 2H, Ar—H), ESI-MS: [M–H]$^-$ calcd for $C_{14}H_9BrFNO$: 304.0, found: 304.0.

4-Bromo-2-(5-chloro-1H-indol-2-yl)phenol (8)

Yield: 16%, $R_f$: 0.17 (hexane/ethyl acetate=3/1), $^1$H NMR (300 MHz, CDCl$_3$): δ 9.44 (s, 1H, Ar—H, J=2.4 Hz), 7.85 (d, 1H, Ar—H, J=2.4 Hz), 7.62 (d, 2H, Ar—H, J=1.8 Hz), 7.38-7.29 (m, 2H, Ar—H), 7.17 (dd, 1H, Ar—H, J=2.1 & 8.7 Hz), 6.82 (d, 2H, Ar—H, J=8.7 Hz), 5.60 (s, 1H, OH), ESI-MS: [M–H]$^-$ calcd for $C_{14}H_9BrClNO$: 322.0, found: 321.8.

2-(5-Bromo-2-hydroxyphenyl)-1H-indole-5-carbonitrile (9)

Yield: 33%, $R_f$: 0.23 (hexane/ethyl acetate=3/1), $^1$H NMR (300 MHz, DMSO-$d_6$): δ 11.84 (s, 1H, NH), 10.65 (s, 1H, OH), 8.07 (s, 1H, Ar—H), 7.95 (d, 1H, Ar—H, J=8.7 Hz), 7.59 (d, 1H, Ar—H, J=8.7 Hz), 7.45-7.32 (m, 2H, Ar—H), 7.22 (s, 1H, Ar—H), 6.98 (d, 1H, Ar—H, J=8.7 Hz), ESI-MS: [M–H]$^-$ calcd for $C_{15}H_9BrN_2O$: 312.9878, found: 312.9980.

4-Bromo-2-(5-(trifluoromethyl)-1H-indol-2-yl)phenol (10)

Yield: 18%, $R_f$: 0.26 (hexane/ethyl acetate=3/1), $^1$H NMR (300 MHz, CDCl$_3$): δ 9.69 (s, 1H, NH), 7.93 (s, 1H Ar—H), 7.87 (d, 1H, Ar—H, J=2.4 Hz), 7.50-7.49 (m, 2H, Ar—H), 7.35-7.27 (m, 1H, Ar—H), 6.95 (s, 1H, Ar—H), 6.80 (d, 1H, Ar—H, J=8.4 Hz), 5.84 (s, 1H, OH), ESI-MS: [M–H]$^-$ calcd for $C_{15}H_9BrF_3NO$: 354.0, found: 354.0.

General Procedure for the Synthesis of 5-substituted-2-(4-hydroxybiphenyl-3-yl)-1H-indole Derivatives Boronic acid (0.17 mmol), cesium carbonate (110 mg, 0.34 mmol in 1 mL water), and Pd(PPh$_3$)$_4$ (10 mg, 0.009 mmol) were added to a solution of indole intermediates (0.17 mmol) in DMF (5 mL). The mixture was allowed to stir at 100° C. for 4 h. Upon cooling to room temperature, the reaction mixture was diluted with water (30 mL) and ethyl acetate (15 mL). The solution pH was adjusted to 7 by using 1 N HCl. The organic phase was dried over MgSO$_4$, filtered, and concentrated under reduced pressure. The resulting residue was purified by column chromatography to provide the corresponding biphenylindole compounds.

3-(1H-Indol-2-yl)-4'-methoxybiphenyl-4-ol (11)

Yield: 12%, $R_f$: 0.24 (hexane/ethyl acetate=3/2), $^1$H NMR (300 MHz, CD$_3$OD): δ 7.78 (d, 1H, Ar—H, J=2.1 Hz), 7.48-7.39 (m, 3H, Ar—H), 7.30 (dd, 1H, Ar—H, J=8.1 & 0.9 Hz), 7.22 (dd, 1H, Ar—H, J=2.4 & 8.4 Hz), 7.00-6.91 (m, 1H, Ar—H), 6.89-6.83 (m, 5H, Ar—H), 3.71 (s, 3H, OCH$_3$), $^{13}$C NMR (75 MHz, CD$_3$OD): δ 158.85, 153.07, 136.52, 135.74, 133.41, 132.78, 128.57, 127.17, 125.98, 125.28, 120.89, 119.48, 119.33, 118.81, 116.33, 113.77, 110.59, 99.68, 54.32 (OCH$_3$), ESI-MS: [M–H]$^-$ calcd for C$_{21}$H$_7$NO$_2$: 314.1, found: 314.0.

3-(5-Fluoro-1H-indol-2-yl)-4'-methoxybiphenyl-4-ol (12)

Yield: 24%, R: 0.39 (hexane/ethyl acetate=3/2), $^1$H NMR (300 MHz, DMSO-d$_6$): δ 11.40 (s, 1H, NH), 7.98 (s, 1H, Ar—H), 7.64 (d, 2H, Ar—H, J=8.4 Hz), 7.48-7.39 (m, 2H, Ar—H), 7.28 (d, 1H, Ar—H, J=9.6 Hz), 7.12-6.87 (m, 4H, Ar—H), 6.77-6.62 (m, 1H, Ar—H), 3.80 (s, 3H, OCH$_3$), $^{13}$C NMR (75 MHz, CD$_3$OD): δ 159.33, 140.76, 133.55, 128.34, 127.56, 127.30, 127.17, 126.21, 126.12, 113.92, 113.83, 54.33 (OCH$_3$), ESI-MS: [M–H]$^-$ calcd for C$_{21}$H$_{16}$FNO$_2$: 332.1, found: 332.0.

4'-Chloro-3-(5-fluoro-1H-indol-2-yl)biphenyl]-4-ol (13)

Yield: 30%, R$_f$: 0.31 (hexane/ethyl acetate=3/2), $^1$H NMR (300 MHz, DMSO-d$_6$): δ 11.41 (s, 1H, NH), 8.06 (s, 1H, Ar—H), 7.76 (d, 2H, Ar—H, J=8.4 Hz), 7.55-7.40 (m, 5H, Ar—H), 7.32-7.26 (m, 1H, Ar—H), 7.14-7.06 (m, 2H, Ar—H), 6.96-6.88 (m, 1H, Ar—H), $^{13}$C NMR (75 MHz, DMSO-d$_6$): δ 154.94, 137.25, 133.45, 131.90, 130.55, 129.18, 128.36, 127.16, 125.91, 117.57, 102.33, ESI-MS: [M–H]$^-$ calcd for C$_{20}$H$_{13}$ClFNO: 336.1, found: 336.1.

3-(5-Chloro-1H-indol-2-yl)-4'-methoxybiphenyl-4-ol (14)

Yield: 20%, R$_f$: 0.18 (hexane/ethyl acetate=3/1), $^1$H NMR (300 MHz, DMSO-d$_6$): δ 11.50 (s, 1H, NH), 7.99 (d, 1H, Ar—H, J=2.1 Hz), 7.64 (d, 2H, Ar—H, J=8.7 Hz), 7.57 (d, 1H, Ar—H, J=8.7 Hz), 7.58-7.39 (m, 2H, Ar—H), 7.10-6.99 (m, 5H, Ar—H), 3.58 (s, 3H, OCH$_3$), $^{13}$C NMR (75 MHz, DMSO-d$_6$): δ 158.79, 154.27, 137.31, 135.15, 132.87, 131.66, 130.03, 127.74, 126.92, 125.42, 123.93, 121.39, 119.25, 118.97, 117.44, 114.67, 113.13, 101.63, 55.62 (OCH$_3$), ESI-MS: [M–H]$^-$ calcd for C$_{21}$H$_{16}$ClNO$_2$: 348.1, found: 347.9.

3-(5-Chloro-1H-indol-2-yl)-3'-nitrobiphenyl-4-ol (15)

Yield: 20%, R$_f$: 0.17 (hexane/ethyl acetate=3/2), $^1$H NMR (300 MHz, CD$_3$OD): δ 8.57 (t, 1H, Ar—H, J=2.1 Hz), 8.19 (dd, 1H, Ar—H, J=1.5 & 8.1 Hz), 8.11-8.06 (m, 3H, Ar—H), 7.69 (t, 1H, Ar—H, J=8.1 Hz), 7.57-7.50 (m, 2H, Ar—H), 7.42 (d, 1H, Ar—H, J=8.7 Hz), 7.01-7.11 (m, 3H, Ar—H), $^{13}$C NMR (75 MHz, CD$_3$OD): δ 155.04, 148.85, 142.52, 136.81, 134.95, 132.24, 130.25, 129.65, 126.84, 125.93, 124.46, 121.07, 120.86, 120.55, 119.47, 118.74, 116.83, 111.84, 100.10, ESI-MS: [M–H]$^-$ calcd for C$_{20}$H$_{13}$ClN$_2$O$_3$: 362.8, found: 362.9.

4'-Chloro-3-(5-chloro-1H-indol-2-yl)biphenyl-4-ol (16)

Yield: 24%, R$_f$: 0.17 (hexane/ethyl acetate=3/1), $^1$H NMR (300 MHz, CDCl$_3$): δ 9.52 (s, 1H, NH), 7.91 (d, 1H, Ar—H, J=2.1 Hz), 7.63 (d, 1H, Ar—H, J=1.8 Hz), 7.54 (d, 2H, Ar—H, J=8.7 Hz), 7.47-7.32 (m, 4H, Ar—H), 7.17 (dd, 1H, Ar—H, J=1.8 & 8.7 Hz), 7.00 (d, 1H, Ar—H, J=8.4 Hz), 6.90 (d, 1H, Ar—H, J=1.2 Hz), $^{13}$C NMR (75 MHz, CD$_3$OD): δ 151.54, 138.73, 136.15, 134.74, 133.86, 133.25, 129.29, 129.00, 128.05, 127.64, 126.86, 125.77, 122.60, 119.75, 119.03, 117.24, 112.02, 99.86, ESI-MS: [M–H]$^-$ calcd for C$_{20}$H$_{13}$Cl$_2$NO: 352.0, found: 351.9.

3-(5-Chloro-1H-indol-2-yl)-4'-fluorobiphenyl-4-ol (17)

Yield: 24%, R$_f$: 0.19 (hexane/ethyl acetate=3/1), $^1$H NMR (300 MHz, CDCl$_3$): δ 10.59 (s, 1H, NH), 8.96 (d, 1H, Ar—H, J=3.0 Hz), 8.71-8.51 (m, 3H, Ar—H), 8.50-8.39 (m, 2H, Ar—H), 8.28-8.18 (m, 3H, Ar—H), 8.06 (d, 1H, Ar—H, J=9.0 Hz), 7.96 (s, 1H), 6.68 (s, 1H, OH), $^{13}$C NMR (75 MHz, CDCl$_3$): δ 163.98, 160.72, 151.37, 136.36, 134.70, 134.07, 129.27, 128.43, 128.32, 127.65, 126.85, 125.70, 122.50, 119.71, 118.89, 117.18, 115.86, 115.57, 111.02, 99.68, ESI-MS: [M–H]$^-$ calcd for C$_{20}$H$_{13}$ClFNO: 335.8, found: 335.9.

3-(5-Chloro-1H-indol-2-yl)biphenyl-4-ol (18)

Yield: 18%, R$_f$: 0.26 (hexane/ethyl acetate=3/2), $^1$H NMR (300 MHz, CD$_3$OD): δ 8.01 (d, 1H, Ar—H, J=2.2 Hz), 7.66 (dd, 2H, Ar—H, J=1.2 & 7.2 Hz), 7.51-7.34 (m, 1H, Ar—H), 7.48-7.39 (m, 4H, Ar—H), 7.27-7.35 (m, 1H, Ar—H), 7.08-6.70 (m, 3H, Ar—H), $^{13}$C NMR (75 MHz, CD$_3$OD): δ 153.74, 140.75, 133.10, 128.37, 126.81, 126.29, 126.17, 125.85, 124.45, 120.91, 118.64, 116.44, 111.81, 99.47, ESI-MS: [M–H]calcd for C$_{20}$H$_{14}$ClNO: 318.1, found: 318.0.

2-(4'-Chloro-4-hydroxy-[1,1'-biphenyl]-3-yl)-1H-indole-5-carbonitrile (19)

Yield: 12%, R: 0.2 (hexane/ethyl acetate=3/1), $^1$H NMR (300 MHz, CD$_3$OD): δ 7.96 (d, 1H, Ar—H, J=2.4 Hz), 7.93 (d, 1H, Ar—H, J=0.9 Hz), 7.60 (d, 2H, Ar—H, J=8.4 Hz), 7.54 (d, 1H, Ar—H, J=8.4 Hz), 7.44-7.29 (m, 4H, Ar—H), 7.11 (s, 1H, Ar—H), 6.95 (d, 1H, Ar—H, J=8.4 Hz), $^{13}$C NMR (75 MHz, CD$_3$OD): δ 155.63, 140.58, 139.66, 139.58, 133.62, 132.95, 129.75, 128.51, 127.19, 126.37, 124.89, 121.90, 119.79, 117.86, 113.10, 102.64, 102.07, ESI-MS: [M–H]$^-$ calcd for C$_{21}$H$_{13}$ClN$_2$O: 343.0716, found: 343.0731.

2-(4-Hydroxy-[1,1'-biphenyl]-3-yl)-1H-indole-5-carbonitrile (20)

Yield: 12%, R$_f$: 0.2 (hexane/ethyl acetate=3/1), $^1$H NMR (300 MHz, CD$_3$OD): δ 8.03 (d, 1H, Ar—H, J=2.1 Hz), 7.99 (d, 1H, Ar—H, J=0.6 Hz), 7.67 (d, 1H, Ar—H, J=1.5 Hz), 7.65 (s, 1H, Ar—H), 7.60 (d, 1H, Ar—H, J=8.4 Hz), 7.50-7.28 (m, 5H, Ar—H), 7.16 (s, 1H, Ar—H), 7.06 (d, 1H, Ar—H, J=8.4 Hz), $^{13}$C NMR (75 MHz, CD$_3$OD): δ 155.69, 142.28, 140.17, 140.02, 134.77, 130.11, 130.07, 129.03, 128.03, 127.84, 127.64, 126.70, 125.20, 122.30, 120, 118.18, 113.47, 102.97, 102.26, ESI-MS: [M–H]$^-$ calcd for C$_{21}$H$_{14}$N$_2$O: 309.1106, found: 309.1108.

4'-Methoxy-3-(5-(trifluoromethyl)-1H-indol-2-yl)biphenyl-4-ol (21)

Yield: 12%, R$_f$: 0.29 (hexane/ethyl acetate=3/1), $^1$H NMR (300 MHz, CD$_3$OD): δ 7.97 (d, 1H, Ar—H, J=2.4 Hz), 7.88 (d, 1H, Ar—H, J=0.9 Hz), 7.59 (d, 3H, Ar—H, J=8.7 Hz), 7.40 (dd, 1H, Ar—H, J=2.4 & 8.4 Hz), 7.36-7.30 (m, 1H, Ar—H), 7.14 (s, 1H, Ar—H), 7.05-6.87 (m, 3H, Ar—H), 3.85 (s, 3H, OCH$_3$), $^{13}$C NMR (75 MHz, CD$_3$OD): δ 158.92, 153.33, 138.03, 137.88, 133.24, 132.87, 127.91, 127.54, 127.19, 126.68, 125.48, 121.29, 120.88, 118.62, 117.21, 117.16, 117.03, 116.97, 116.40, 113.80, 111.04, 100.56, 54.33 (OCH$_3$), ESI-MS: [M–H]$^-$ calcd for C$_{22}$H$_{16}$F$_3$NO$_2$: 382.1, found: 382.1.

(Z)-2-(5-Bromo-2-hydroxyphenyl)-N'-hydroxy-1H-indole-5-carboximidamide (22)

Hydroxylamine hydrochloride (0.71 g, 10.2 mmol) and sodium carbonate (0.55 g, 5.1 mmol) were added to a solution of Compound 9 (0.37 g, 1.2 mmol) in ethanol (20 mL). The mixture was allowed to stir at 90° C. for 7 h. After completion of the reaction, the excess solvent was removed under reduced pressure. To the resulting residue were added water (25 mL) and ethyl acetate (25 mL). The combined organic layer was dried over MgSO$_4$, and filtered, and concentrated under reduced pressure. Purification by silica-gel column chromatography afforded Compound 22.

Yield: 60%, R$_f$: 0.12 (Hexane/ethyl acetate=3/1), $^1$H NMR (300 MHz, DMSO-d$_6$): δ 11.37 (s, 1H, OH), 9.39 (s, 1H, NH), 8.22 (s, 1H, Ar—H), 7.93 (d, 1H, Ar—H, J=2.4 Hz), 7.83 (d, 1H, Ar—H, J=1.2 Hz), 7.49-7.38 (m, 2H, Ar—H), 7.28 (dd, 1H, Ar—H, J=2.4 & 8.4 Hz), 7.1 (s, 1H, Ar—H), 6.94 (d, 1H, Ar—H, J=8.7 Hz), 5.71 (s, 2H, NH$_2$), ESI-MS: [M–H]$^-$ calcd for C$_{13}$H$_{12}$BrN$_3$O$_2$: 344.0, found: 343.9.

4-Bromo-2-(5-(5-methyl-1,2,4-oxadiazol-3-yl)-1H-indol-2-yl)phenol (23)

Sodium ethoxide (90 mg, 1.32 mmol) and ethyl acetate (1 mL) were added to a solution of Compound 22 (0.23 g, 0.69 mmol) in ethanol (9 mL). The mixture was allowed to stir at 90° C. for 2 h. After completion of the reaction, the excess solvent was removed under reduced pressure. To the resulting residue were added water (25 mL) and ethyl acetate (25 mL). The combined organic layer was dried over MgSO$_4$, and filtered, and concentrated under reduced pressure. Purification by silica-gel column chromatography afforded Compound 23.

Yield: 42%, R$_f$: 0.25 (Hexane/ethyl acetate=3/1), $^1$H NMR (300 MHz, DMSO-d$_6$): δ 11.61 (s, 1H, NH), 10.59 (s, 1H, OH), 8.22 (s, 1H, Ar—H), 7.95 (d, 1H, Ar—H, J=2.4 Hz), 7.74 (dd, 1H, Ar—H, J=1.5 & 8.4 Hz), 7.58 (d, 1H, Ar—H, J=8.4 Hz), 7.33 (dd, 1H, Ar—H, J=2.4 & 8.7 Hz), 7.21 (s, 1H, Ar—H), 6.97 (d, 1H, Ar—H, J=8.7 Hz), 2.66 (s, 3H, CH$_3$), ESI-MS: [M–H]$^-$ calcd for C$_{17}$H$_{12}$BrN$_3$O$_2$: 368.0, found: 368.0.

General Procedure for the Synthesis of 3-(5-(5-methyl-1,2,4-oxadiazol-3-yl)-1H-indol-2-yl)biphenyl-4-ol Derivatives Boronic acid (0.27 mmol), cesium carbonate (0.55 mmol), and Pd(PPh$_3$)$_4$ (0.014 mmol) were added to a solution of Compound 23 (0.27 mmol) as an intermediate in DMF (5 mL). The mixture was allowed to stir at 100° C. for 4 h. Upon cooling to room temperature, the reaction mixture was diluted with water (30 mL) and ethyl acetate (15 mL). The solution pH was adjusted by using 1 N HCl. The organic phase was dried over MgSO$_4$, filtered, and concentrated under reduced pressure. The resulting residue was purified by column chromatography to provide the corresponding compounds.

4'-Chloro-3-(5-(5-methyl-1,2,4-oxadiazol-3-yl)-1H-indol-2-yl)biphenyl-4-ol (24)

Yield: 30%, R$_f$: 0.25 (Hexane/ethyl acetate=3/1), ESI-MS: [M–H]$^-$ calcd for C$_{23}$H$_{16}$ClN$_3$O$_2$: 400.1, found: 400.1.

2-(6-(5-Methyl-1,2,4-oxadiazol-3-yl)-1H-indol-2-yl)-4-(thiophen-3-yl)phenol (25)

Yield: 33%, R$_f$: 0.25 (Hexane/ethyl acetate=3/1), ESI-MS: [M–H]$^-$ calcd for C$_{21}$H$_{11}$N$_3$O$_2$S: 372.1, found: 372.0.

4'-Fluoro-3-(5-(5-methyl-1,2,4-oxadiazol-3-yl)-1H-indol-2-yl)biphenyl-4-ol (27)

Yield: 34%, R$_f$: 0.27 (Hexane/ethyl acetate=3/1), ESI-MS: [M–H]$^-$ calcd for C$_{23}$H$_{16}$FN$_3$O$_2$: 384.1, found: 384.1.

tert-Butyl (4'-hydroxy-3'-(5-(5-methyl-1,2,4-oxadiazol-3-yl)-1H-indol-2-yl)biphenyl-4-yl)methylcarbamate (28)

Yield: 32%, R$_f$: 0.31 (Hexane/ethyl acetate=3/2), $^1$H NMR (300 MHz, DMSO-d$_6$): 11.63 (s, 1H, NH), 10.39 (s, 1H, OH), 8.22 (s, 1H, Ar—H), 8.07 (d, 1H, Ar—H, J=2.4 Hz), 7.76-7.64 (m, 3H, Ar—H), 7.59 (d, 1H, Ar—H, J=8.4 Hz), 7.51-7.42 (m, 2H, Ar—H), 7.32 (d, 2H, Ar—H, J=8.1 Hz), 7.23 (s, 1H, Ar—H), 7.10 (d, 1H, Ar—H, J=8.4 Hz), 4.17 (d, 2H, J=6.0 Hz, CH$_2$), 2.66 (s, 3H, OCH$_3$), 1.41 (s, 9H, (CH$_3$)$_3$), ESI-MS: [M–H]$^-$ calcd for C$_{29}$H$_{28}$N$_4$O$_4$: 495.2, found: 495.2.

3-(5-(5-Methyl-1,2,4-oxadiazol-3-yl)-1H-indol-2-yl)biphenyl-4-ol (29)

Yield: 37%, R$_f$: 0.23 (Hexane/ethyl acetate=3/1), ESI-MS: [M–H]$^-$ calcd for C$_{23}$H$_7$N$_3$O$_2$: 366.1, found: 366.1.

4'-Methoxy-3-(5-(5-methyl-1,2,4-oxadiazol-3-yl)-1H-indol-2-yl)-[1,1'-biphenyl]-4-ol (30)

Yield: 36%, R$_f$: 0.27 (Hexane/ethyl acetate=3/1), ESI-MS: [M–H]$^-$ calcd for C$_{24}$H$_{19}$N$_3$O$_3$: 396.1, found: 396.2.

3-(5-(5-Methyl-1,2,4-oxadiazol-3-yl)-1H-indol-2-yl)-4'-(trifluoromethyl)-[1,1'-biphenyl]-4-ol (31)

Yield: 39%, R$_f$: 0.26 (Hexane/ethyl acetate=3/1), ESI-MS: [M–H]$^-$ calcd for C$_{24}$H$_6$F$_3$N$_3$O$_2$: 434.1, found: 434.1.

General Procedure for the Synthesis of 2-(4'-chloro-4-hydroxybiphenyl-3-yl)-1H-indole-5-carboximidamide Derivatives A catalytic amount of Raney-Ni was added to a solution of oxadiazole intermediates in methanol/acetic acid (10 mL, 7/1). The mixture was allowed to react in a hydrogenation reactor at 50 psi for 5 h. After addition of cesium carbonate (0.55 mmol) and Pd(PPh$_3$)$_4$ (0.014 mmol), the reaction mixture was filtered through Celite and concentrated under reduced pressure. Purification by HPLC afforded the final compounds.

2-(4'-Chloro-4-hydroxybiphenyl-3-yl)-1H-indole-5-carboximidamide (32)

HPLC: 80/20 water/acetonitrile (0.1% formic acid), flow rate 2 mL/min, RT: 9.15 min, Yield: 22%, $^1$H NMR (300

MHz, CD₃OD): δ 8.58 (s, 2H, NH₂), 8.11 (s, 1H, Ar—H), 8.01 (d, 1H, Ar—H, J=2.4 Hz), 7.67-7.57 (m, 3H, Ar—H), 7.54-7.45 (m, 1H, Ar—H), 7.45-7.25 (m, 4H, Ar—H), 6.99 (d, 1H, Ar—H, J=8.4 Hz), $^{13}$C NMR (75 MHz, CD₃OD): δ 168.92, 168.03, 158.67, 140.43, 139.78, 139.22, 131.78, 129.40, 128.60, 128.37, 127.37, 127.30, 125.45, 120.19, 119.33, 118.53, 117.93, 111.33. ESI-MS: [M+H]⁺ calcd for $C_{21}H_{16}ClN_3O$: 362.1, found: 362.1.

2-(2-Hydroxy-5-(thiophen-2-yl)phenyl)-1H-indole-5-carboximidamide (33)

HPLC: 70/30 water/acetonitrile (0.1% formic acid), flow rate 2 mL/min; RT=8.71 min, Yield: 37%, $^1$H NMR (300 MHz, CD₃OD): δ 8.58 (s, 4H), 8.14 (s, 1H, Ar—H), 8.04 (d, 1H, Ar—H, J=2.1 Hz), 7.66 (d, 1H, Ar—H, J=8.4 Hz), 7.56-7.50 (m, 1H, Ar—H), 7.47 (dd, 1H, Ar—H, J=2.4 & 8.4 Hz), 7.37-7.28 (m, 2H, Ar—H), 7.19 (s, 1H, Ar—H), 7.13-7.04 (m, 1H, Ar—H), 7.00 (d, 1H, Ar—H, J=8.4 Hz), $^{13}$C NMR (75 MHz, CD₃OD): δ 168.99, 167.98, 154.86, 144.01, 139.61, 138.61, 128.45, 127.59, 126.45, 124.78, 123.34, 121.80, 120.54, 119.79, 118.51, 118.22, 116.90, 111.54, ESI-MS: [M−H]⁻ calcd. for $C_{19}H_{15}N_3OS$: 332.1, found: 332.0.

2-(2-Hydroxyphenyl)-1H-indole-5-carboximidamide (34)

HPLC: Acetonitrile (A)/water (B) (0.1% formic acid), The gradient consisted of 10% A to 90% A in 30 min at 2 mL/min flow rate. RT=9.78 min, Yield: 46%, $^1$H NMR (300 MHz, CD₃CN/D₂O): δ 8.48 (s, 1H, NH), 8.18 (s, 1H, Ar—H), 7.88 (d, 1H, Ar—H, J=7.8 Hz), 7.73 (d, 1H, Ar—H, J=8.7 Hz), 7.65-7.56 (m, 1H, Ar—H), 7.39-7.29 (m, 1H, Ar—H), 7.12 (s, 1H, Ar—H), 7.15-6.95 (m, 2H, Ar—H), $^{13}$C NMR (75 MHz, CD₃CN/D₂O): δ 170.52, 167.61, 154.28, 139.82, 139.29, 130.23, 128.61, 121.63, 121.43, 121.04, 120.88, 118.22, 117.18, 112.62, 101.09, ESI-MS: [M−H]⁻ calcd for $C_{15}H_3N_3O$: 250.1, found: 250.0.

2-(4'-Fluoro-4-hydroxybiphenyl-3-yl)-1H-indole-5-carboximidamide (35)

HPLC: Acetonitrile (A)/water (B) (0.1% formic acid), the gradient consisted of 40% A to 50% A in 30 min at 2 mL/min flow rate, RT=9.78 min. Yield: 30%, $^1$H NMR (300 MHz, CD₃OD): δ 8.14 (s, 1H, Ar—H), 8.03 (d, 1H, Ar—H, J=2.1 Hz), 7.68-7.60 (m, 3H, Ar—H), 7.57-7.45 (m, 2H, Ar—H), 7.37 (d, 1H, Ar—H, J=8.1 Hz), 7.22 (s, 1H, Ar—H), 7.06 (d, 1H, Ar—H, J=8.4 Hz), $^{13}$C NMR (75 MHz, CD₃OD): δ 167.95, 163.79, 154.07, 139.67, 138.65, 137.00, 132.10, 128.56, 128.49, 128.00, 127.90, 127.33, 125.88, 120.60, 119.83, 118.40, 118.19, 116.55, 115.17, 114.89, 111.53, 101.26, ESI-MS: [M+H]⁺ calcd for $C_{21}H_{16}FN_3O$: 346.1, found: 346.0.

tert-Butyl (3'-(5-carbamimidoyl-1H-indol-2-yl)-4'-hydroxybiphenyl-4-yl)methylcarbamate (36)

HPLC: 70/30 water/acetonitrile (0.1% formic acid), flow rate 2 mL/min; RT=5.94 min, Yield: 40%, $^1$H NMR (300 MHz, CD₃OD): δ 8.14 (s, 1H, Ar—H), 8.00 (d, 1H, Ar—H, J=2.1 Hz), 7.71-7.63 (m, 3H, Ar—H), 7.57-7.52 (m, 1H, Ar—H), 7.45 (dd, 1H, Ar—H, J=2.1 & 8.4 Hz), 7.24-7.14 (m, 3H, Ar—H), 7.07 (d, 1H, Ar—H, J=8.4 Hz) 4.23 (s, 2H, CH₂), 1.49 (s, 9H, (CH₃)₃), $^{13}$C NMR (75 MHz, CD₃OD): δ 167.97, 157.22, 154.03, 139.68, 139.33, 138.77, 138.12, 132.80, 128.59, 128.51, 127.34, 127.25, 126.19, 125.83, 120.58, 119.79, 118.34, 118.16, 116.51, 111.52, 101.20, 78.82, 43.35 (CH₂), 27.38 (CH₃)₃, ESI-MS: [M+H]⁺ calcd. for $C_{27}H_{28}N_4O_3$: 457.2, found: 457.1.

2-(4'-(Aminomethyl)-4-hydroxy-[1,1'-biphenyl]-3-yl)-1H-indole-5-carboximidamide (37)

Compound 36 was dissolved in TFA/dichlormethane (5 mL, 1/1). The solution was allowed to stir at room temperature for 1 h. The reaction solution was concentrated under reduced pressure. Purification by HPLC afforded the title compound.

HPLC: 70/30 water/acetonitrile (0.1% formic acid), flow rate 2 mL/min, RT=2.56 min. Yield: 72%, $^1$H NMR (300 MHz, CD₃CN/D₂O): δ 8.49 (d, 2H, Ar—H, J=7.2 Hz), 8.14 (d, 1H, Ar—H, J=8.1 Hz), 8.06 (d, 1H, Ar—H, J=8.7 Hz), 8.01-7.87 (m, 4H, Ar—H), 7.61 (s, 1H, Ar—H), 7.53 (d, 1H, Ar—H, J=8.4 Hz), 4.54 (s, 2H, CH₂), $^{13}$C NMR (75 MHz, CD₃CN/D₂O): δ 167.57, 161.90, 154.34, 141.20, 139.86, 132.61, 131.91, 130.12, 128.62, 127.50, 126.89, 121.53, 121.05, 117.79, 112.66, 101.63, 43.15 (CH₂), ESI-MS: [M−H]⁻ calcd. for $C_{22}H_{20}N_4O$: 355.1, found: 355.2.

2-(4-Hydroxy-[1,1'-biphenyl]-3-yl)-1H-indole-5-carboximidamide (38)

HPLC: 72/28 water/acetonitrile (0.1% formic acid), flow rate 2 mL/min, RT=8.62 min. Yield: 42%, $^1$H NMR (300 MHz, CD₃CN/D₂O): δ 8.76 (s, 1H, NH), 8.48 (s, 1H, Ar—H), 8.43 (s, 1H, Ar—H), 8.10-7.97 (m, 3H, Ar—H), 7.96-7.80 (m, 5H, Ar—H), 7.78-7.70 (m, 1H, Ar—H), 7.57 (s, 1H, Ar—H), 7.49 (d, 1H, Ar—H, J=8.4 Hz), $^{13}$C NMR (75 MHz, CD₃CN/D₂O): δ 153.94, 140.49, 139.78, 138.84, 134.31, 133.52, 131.24, 129.45, 128.29, 127.57, 127.36, 126.91, 126.77, 121.41, 120.94, 117.67, 112.98, ESI-MS: [M+H]⁺ calcd. for $C_{21}H_{17}N_3O$: 328.1, found: 328.2.

2-(4-Hydroxy-4'-methoxy-[1,1'-biphenyl]-3-yl)-1H-indole-5-carboximidamide (39)

HPLC: 75/25 water/acetonitrile (0.1% formic acid), flow rate 2 mL/min, RT=12.98 min. Yield: 33%, $^1$H NMR (300 MHz, CD₃CN/D₂O): δ 8.48 (s, 1H, NH), 8.19 (s, 1H, Ar—H), 8.08 (d, 1H, Ar—H, J=2.4 Hz), 7.80-7.68 (m, 3H, Ar—H), 7.65-7.52 (m, 2H, Ar—H), 7.29 (s, 1H, Ar—H), 7.22-7.10 (m, 3H, Ar—H), 6.92-6.82 (m, 1H, Ar—H), 3.85 (s, 3H, OCH₃), $^{13}$C NMR (75 MHz, CD₃CN/D₂O): δ 172.68, 169.92, 161.54, 156.06, 142.12, 135.61, 135.43, 130.91, 130.83, 130.41, 128.58, 123.75, 123.23, 120.0, 118.67, 117.63, 117.11, 114.88, 103.69, 57.94 (OCH₃), ESI-MS: [M+H]⁺ calcd. for $C_{22}H_{19}N_3O_2$: 358.1, found: 358.2.

2-(4-Hydroxy-4'-(trifluoromethyl)-[1,1'-biphenyl]-3-yl)-1H-indole-5-carboximidamide (40)

HPLC: 68/32 water/acetonitrile (0.1% formic acid), flow rate 2 mL/min. RT=9.92 min. Yield: 28%, $^1$H NMR (300 MHz, CD₃CN/D₂O): δ 8.53 (s, 2H, Ar—H), 8.29 (d, 2H, Ar—H, J=7.5 Hz), 8.19 (d, 2H, Ar—H, J=7.8 Hz), 8.12-7.90 (m, 4H, Ar—H), 7.63 (s, 1H, Ar—H), 7.56 (d, 1H, Ar—H, J=8.4 Hz), $^{13}$C NMR (75 MHz, CD₃CN/D₂O): δ 167.59, 154.84, 144.48, 139.88, 131.86, 128.79, 127.48, 127.22, 126.28, 121.56, 121.10, 117.88, 112.68, 101.78, ESI-MS: [M+H]⁺ calcd. for $C_{22}H_{16}F_3N_3O$: 396.1, found: 396.1.

Example 2: Evaluation of the Ability of the Compounds to Inhibit Cell Proliferation MCF7, STK32C/MCF7 cell ($1\times10^4$/well) culture was plated in each well of a 96-well plate until it reached a final volume of 100 μl. After 24 h, the compounds at given concentrations were added. 24 h after the addition, 10 μl of an analytical reagent was plated in each well without bubbling. The reaction was allowed to proceed under basic culture conditions for 30 min to 1 h and the inhibitions of cell proliferation were measured at 450 nm.

FIGS. 3 to 6 show concentration-dependent inhibitions of proliferation of the YANK-expressed cells by treatment with the phenol derivatives of Formulae 7, 9, 13, and 32 (corresponding to Compound 34 in FIG. 2), respectively. Referring to FIGS. 3 to 6, the inventive compounds inhibited the proliferation of the YANK-expressed cells with high efficacy with increasing concentration.

Example 3: Evaluation of the Ability of the Compounds to Inhibit Kinase In Vitro Transduction was performed to overexpress YANK3-HA and YB1-HA genes in cells. Lipofectamine reagent (Invitrogen) was used for gene introgression. When cells were grown to a confluency of 60% in a culture dish, human YANK3-HA and YB1-HA genes were introduced into MCF7 cells. After 48 h, the gene-transfected cells were used for experiments. All cultured cells were harvested, lysed in a lysis buffer (1×RIPA buffer 1 mL, 1 mM PMSF, 1 mg/mL aprotinin, 1 mg/mL leupeptin, 2 mM DTT) for 30 min, and centrifuged at 15,000 rpm and 4° C. for 30 min. The supernatant was collected and its total protein content was quantified by the Bradford method. After YB1-HA gene introgression, the MCF7 cells were treated with each compound (10 mM) at 37° C. for 1 h. 1 μg of anti-HA antibody was cultured with 1000 mg of protein at 4° C. for 15 h, 20 μL of protein A/G-Sepharose was added thereto, followed by culture for another 2 h. The culture was centrifuged to precipitate the protein A/G-Sepharose, washed with IP kinase buffer (50 mM HEPES, pH 7.5, 10 mM $MgCl_2$, 1 mM dithiothreitol, 2.5 mM EGTA, 1 mM NaF, 0.1 mM $Na_3VO_4$), and sufficiently mixed with 20 μL of IP kinase buffer. The kinase reaction was initiated by the addition of 10 mCi of [$\gamma$-$^{32}$P]ATP to 40 μL of IP kinase buffer. The reaction was allowed to proceed at 30° C. for 30 min. After addition of 5 μL of 2×SDS sample buffer, the reaction was quenched by boiling for 5 min, which was confirmed by SDS-PAGE electrophoresis and autoradiography.

Figure 7:
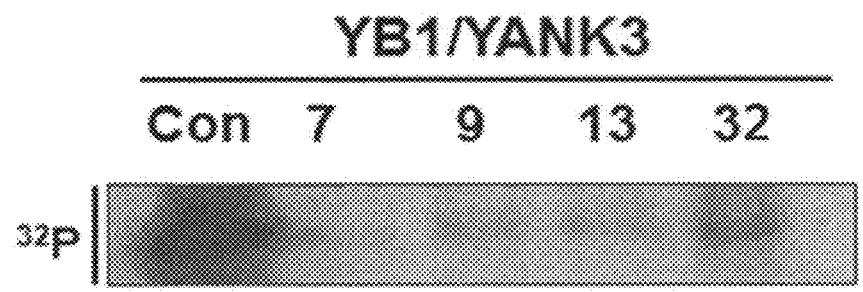
FIG. 7 shows inhibitions of YANK phosphorylation by treatment with the phenol derivatives of Formulae 7, 9, 13 and 32.

Table 1 shows the inhibitions (%) of YANK3 phosphorylation by the phenol derivatives of Formulae 7, 9, 11, 13, 16, 32 (corresponding to Compound 34 in FIG. 2), and 33 (corresponding to Compound 35 in FIG. 2). FIG. 7 shows autoradiographs taken after treatment with the phenol derivatives of Formulae 7, 9, 13, and 32 (corresponding to Compound 34 in FIG. 2).

TABLE 1

| Compound | Inhibition, % |
|---|---|
| 7 | 74 |
| 9 | 144 |
| 11 | 163 |
| 13 | 93 |
| 16 | 125 |
| 32 | 65 |
| 33 | 30 |

As can be seen from the results in Table 1 and FIG. 7, the inventive compounds effectively inhibited the proliferation, migration, and infiltration of YANK-expressed cells, which are known to play a key role in carcinogenesis. These results demonstrate that the inventive compounds can be effectively utilized as basic prophylactic and therapeutic agents for cancer diseases.

What is claimed is:

1. A compound represented by Formula 1:

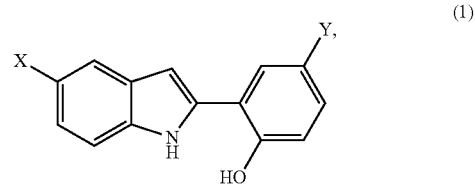

(1)

wherein:

X is selected from the group consisting of hydrogen, halogen, a cyano group, a trifluoromethyl ($CF_3$) group, an amidine (C(=NH)$NH_2$) group, and a 5-methyl-1,2,4-oxadiazole group, Y is selected from the group consisting of hydrogen, halogen, a phenyl group substituted with one or two substituents selected from the group consisting of halogen, methoxy, nitro, trifluoromethyl, aminomethyl, CO—R', COOR', OH, O—R', and NH—R', each R' is independently selected from the group consisting of $C_1$-$C_{18}$ alkyl, alkenyl, alkynyl, and —Z-alkyl, wherein Z is a heteroatom selected from the group consisting of O, S, and N or is —(CH$_2$)$_m$—, and m is an integer from 0 to 5, provided that:

when Y is hydrogen or halogen-, X is not hydrogen, and when Y is hydrogen, X is not an amidine group or a cyano group.

2. The compound according to claim 1, wherein the compound of Formula 1 is represented by Formula 2:

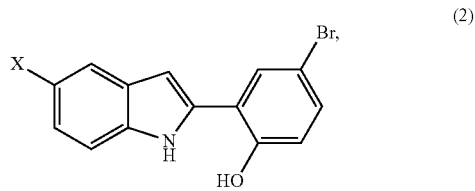

(2)

wherein X is selected from the group consisting of F, Cl, CN, and $CF_3$.

3. A compound represented by Formula 3:

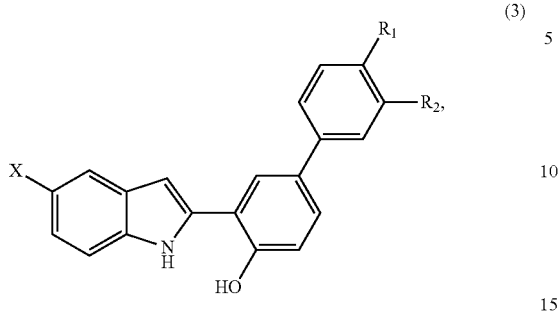

wherein X is selected from the group consisting of H, F, Cl, CN, and CF$_3$, R$_1$ is selected from the group consisting of H, F, Cl, and OCH$_3$, and R$_2$, is H or NO2; wherein at least on selected from the group consisting of X, R1 and R2 is not H.

4. The compound according to claim 1, wherein the compound of Formula 1 is represented by Formula 4:

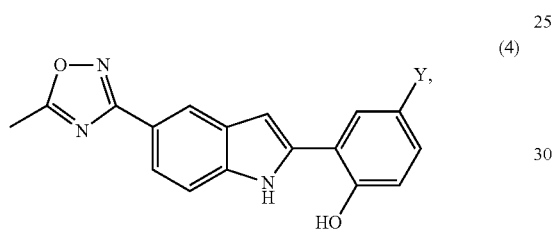

wherein Y is selected from the group consisting of hydrogen, halogen, a phenyl group substituted with one or two substituents selected from the group consisting of halogen, methoxy, nitro, trifluoromethyl, aminomethyl, CO—R', COOR', OH, O—R', and NH—R', each R' is independently selected from the group consisting of C$_1$-C$_{18}$ alkyl, alkenyl, alkynyl, and —Z-alkyl, wherein Z is a heteroatom selected from the group consisting of O, S, and N or is —(CH$_2$)$_m$—, and m is an integer from 0 to 5.

5. The compound according to claim 1, wherein the compound of Formula 1 is represented by Formula 5:

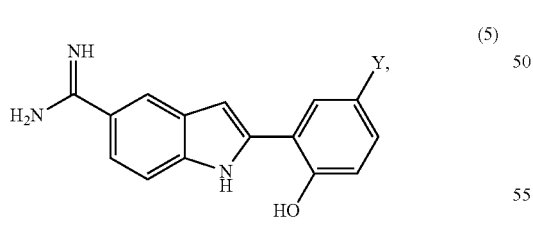

wherein Y is selected from the group consisting of halogen, a phenyl group substituted with one or two substituents selected from the group consisting of halogen, methoxy, nitro, trifluoromethyl, aminomethyl, CO—R' COOR', OH, O—R', and NH—R', each R' is independently selected from the group consisting of C$_1$-C$_{18}$ alkyl, alkenyl, alkynyl, and —Z-alkyl, wherein Z is a heteroatom selected from the group consisting of O, S, and N or is —(CH$_2$)$_m$—, and in is an integer from 0 to 5.

6. A compound represented by a formula selected from the group consisting of Formulae 7 to 31 and 33 to 37:

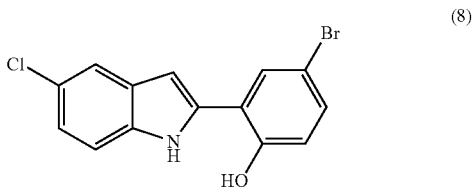

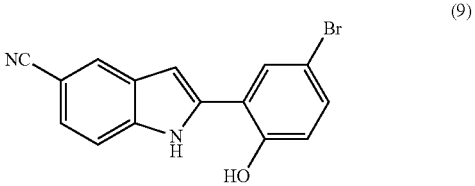

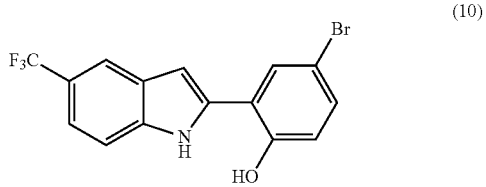

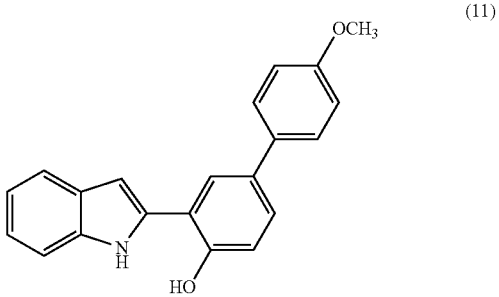

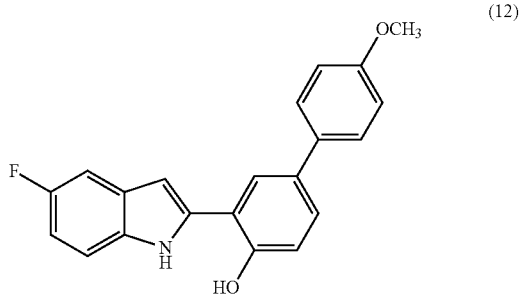

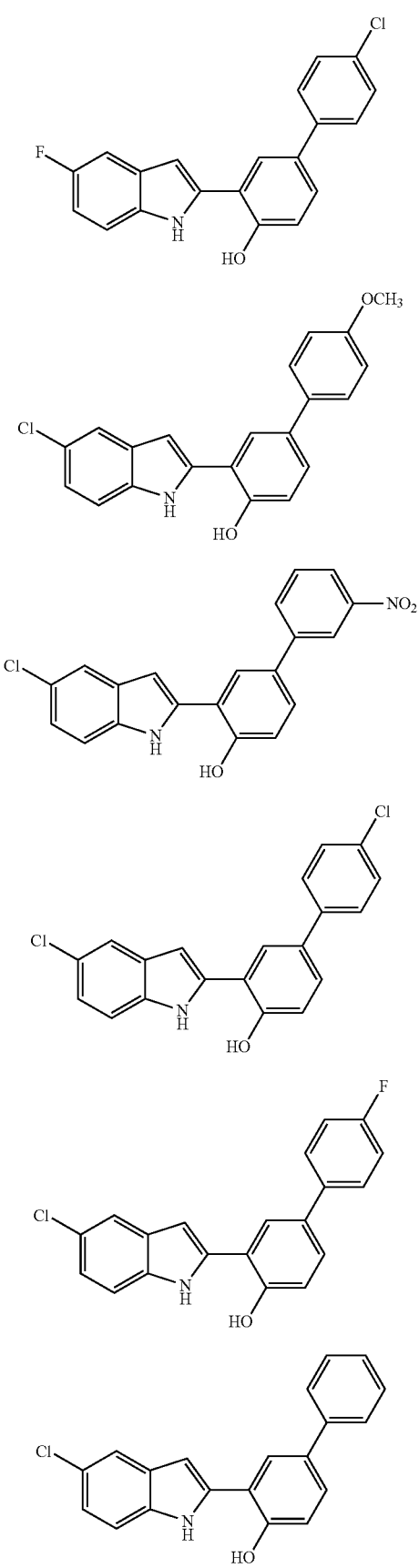
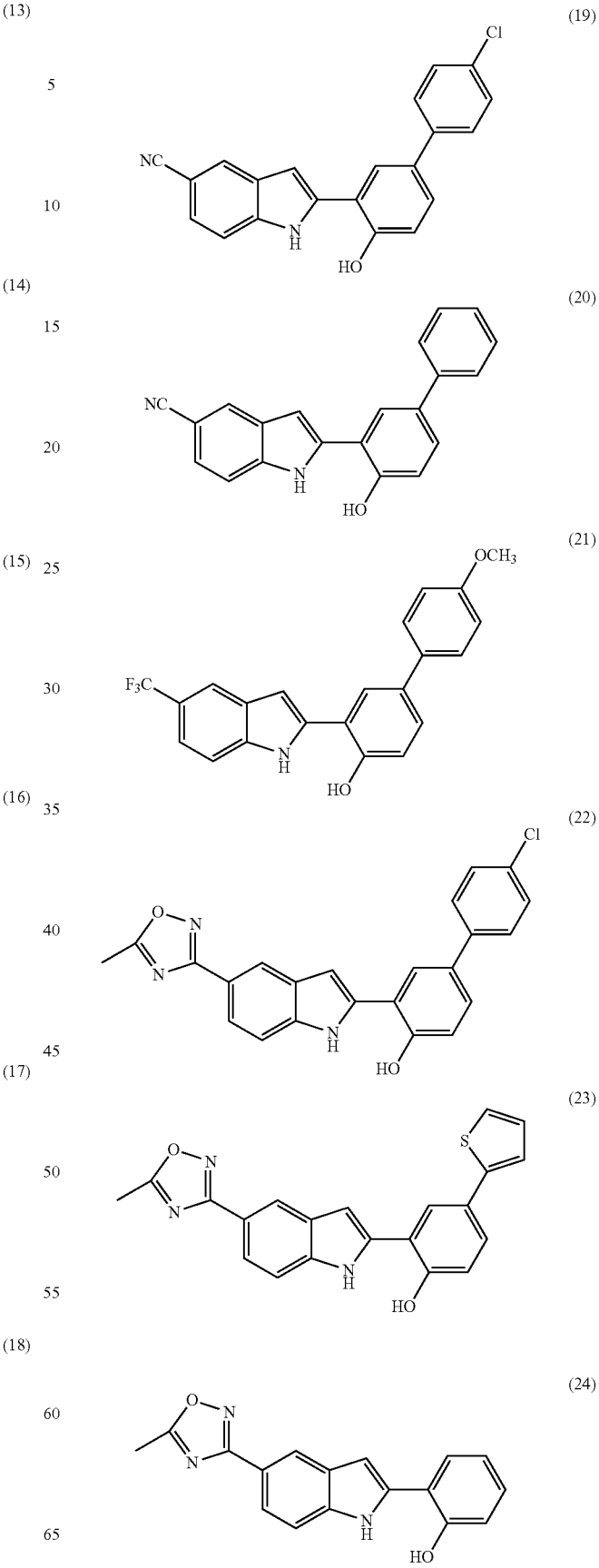

(25)
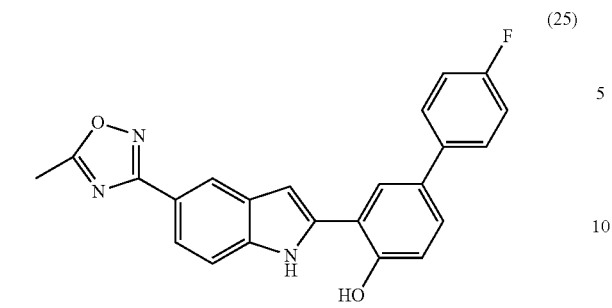
(26)
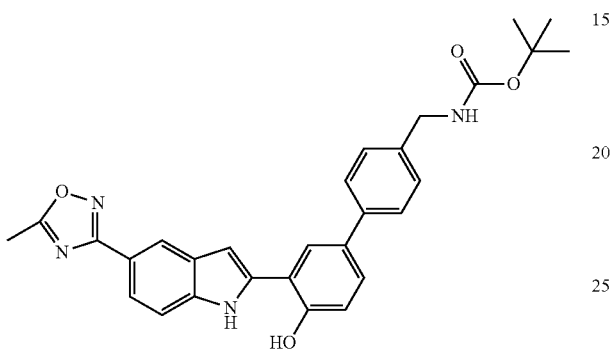
(27)
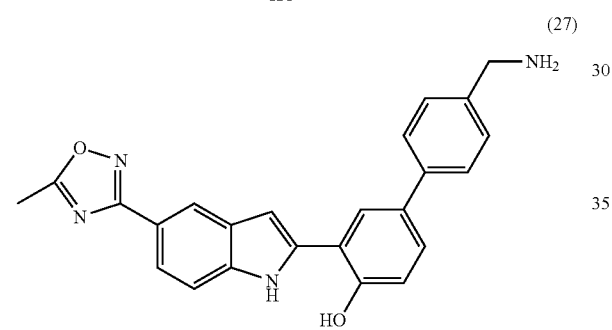
(28)
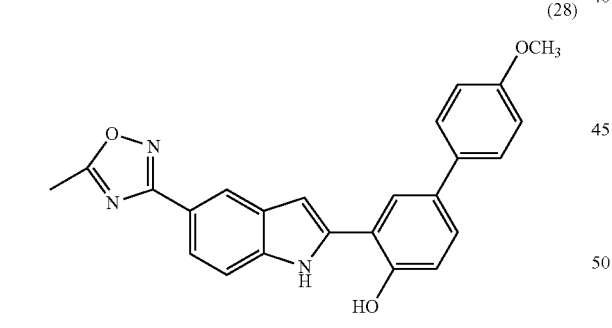
(29)
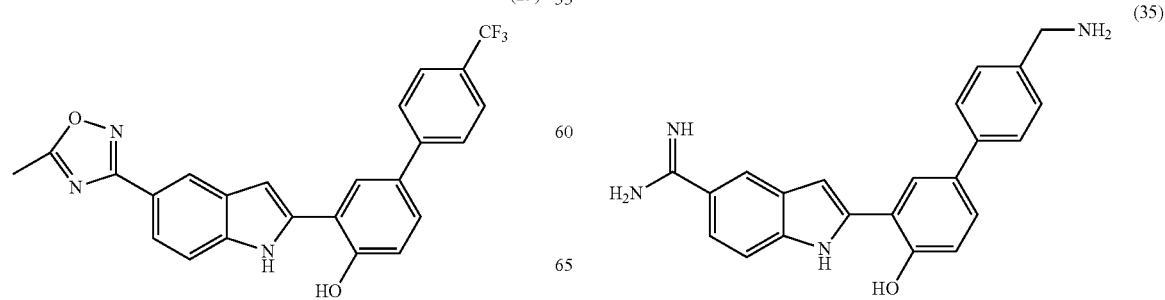
(30)
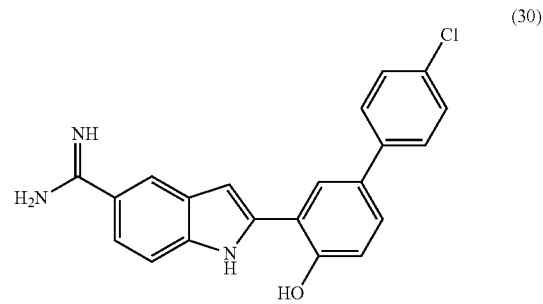 [SMILES: N=C(N)c1ccc2[nH]c(-c3cc(-c4ccc(C(F)(F)F)cc4)ccc3O)cc2c1]
(31)
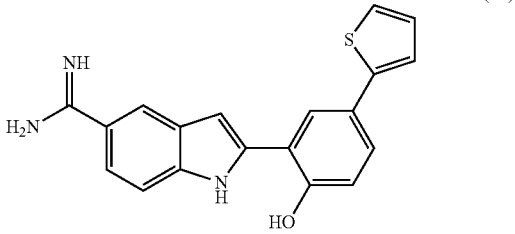
(33)
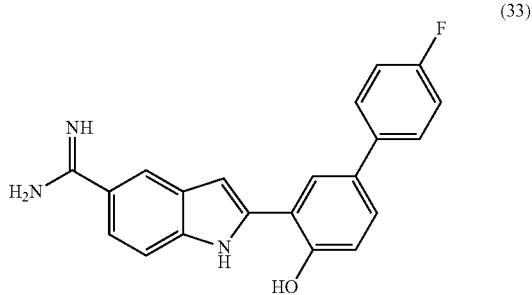
(34)
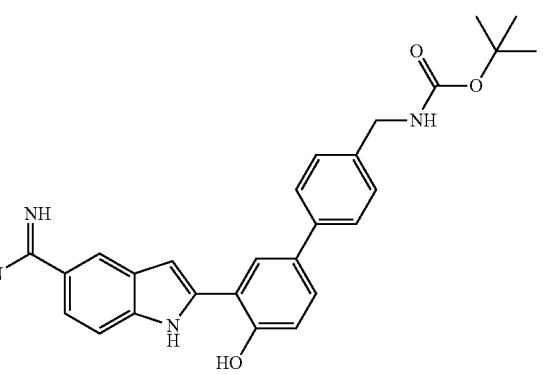
(35)
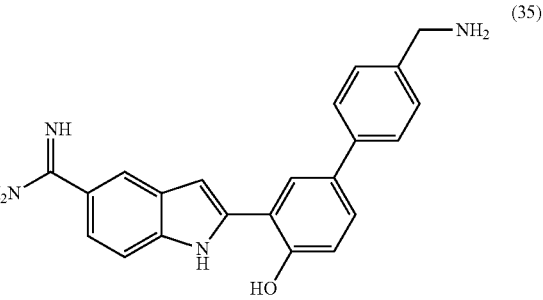

-continued

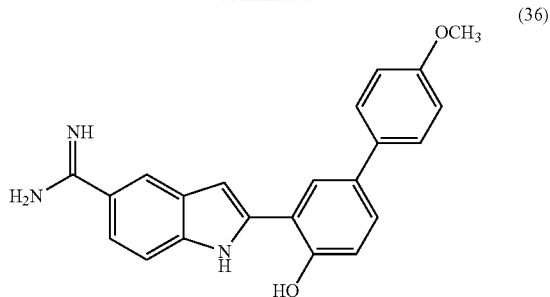

(36)

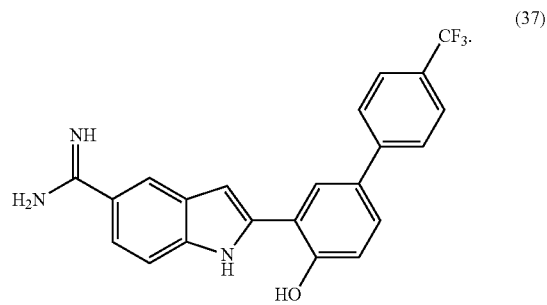 [SMILES: N=C(N)c1ccc2[nH]c(-c3cc(-c4ccc(C(F)(F)F)cc4)ccc3O)cc2c1]

(37)

7. A pharmaceutical composition for inhibiting cell proliferation and migration comprising the compound according to claim 1 or a pharmaceutically acceptable salt thereof as an active ingredient.

8. The pharmaceutical composition according to claim 7, further comprising one or more ingredients selected from the group consisting of excipients, diluents, adjuvants, and stabilizers.

9. The pharmaceutical composition according to claim 8, comprising one or more of the stabilizers, wherein the stabilizers are selected from the group consisting of proteins, carbohydrates, buffers, and mixtures thereof.

10. A method for preparing the compound of claim 1, represented by Formula 1:

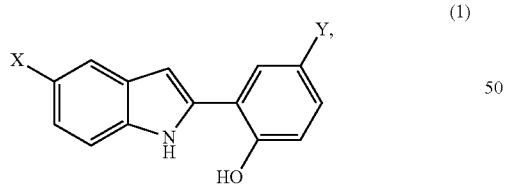

(1)

wherein X is an amidine (C(=NH)NH$_2$) or 5-methyl-1,2,4-oxadiazole group, Y is selected from the group consisting of hydrogen, halogen, a phenyl group substituted with one or two substituents selected from the group consisting of halogen, methoxy, nitro, trifluoromethyl, and aminomethyl, CO—R', COOR', OH, O—R', and NH—R', each R' is independently selected from the group consisting of C$_1$-C$_{18}$ alkyl, alkenyl, alkynyl, and —Z— alkyl, wherein Z is a heteroatom selected from the group consisting of O, S, and N or is —(CH$_2$)$_m$—, and m is an integer from 0 to 5, the method comprising:

reacting the compound of Formula 43:

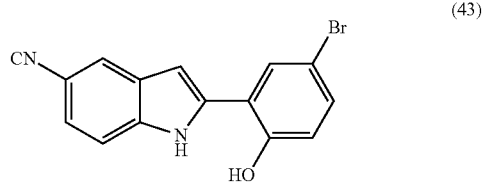

(43)

with NH$_2$OH.HCl, Na$_2$CO$_3$, and ethanol to prepare the compound of Formula 44:

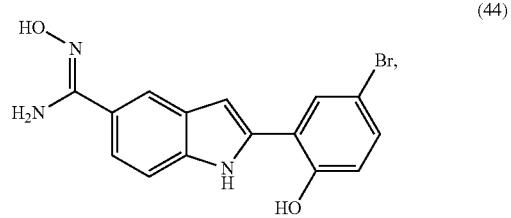 [SMILES: N/C(=N\O)c1ccc2[nH]c(-c3cc(Br)ccc3O)cc2c1]

(44)

reacting the compound of Formula 44 with NaOCH$_2$CH$_3$, ethanol, and ethyl acetate to prepare the compound of Formula 45:

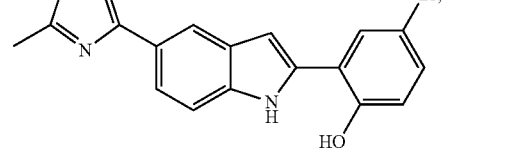

(45)

reacting the compound of Formula 45 with a compound of Formula 46:

(46)

wherein Y is selected from the group consisting of hydrogen, halogen, a phenyl group substituted with one or two substituents selected from the group consisting of halogen, methoxy, nitro, trifluoromethyl, and aminomethyl, CO—R', COOR' OH, O—R', and NH—R', each R' is independently selected from the group consisting of C$_1$-C$_{18}$ alkyl, alkenyl, alkynyl, and —Z-alkyl, wherein Z is a heteroatom selected from the group consisting of O, S, and N or is —(CH$_2$)$_m$—, and m is an integer from 0 to 5, to prepare a compound of Formula 47:

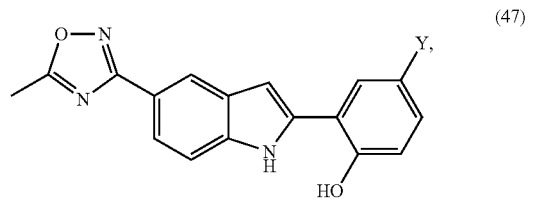
(47)
wherein Y is as defined in Formula 46, and reducing the compound of Formula 47.
* * * * *